United States Patent
Barrera et al.

(10) Patent No.: US 11,666,270 B2
(45) Date of Patent: Jun. 6, 2023

(54) PERSONALIZED AND CONTEXTUALIZED TREATMENT OF SLEEP APNEA AND OBESITY COMORBIDITY

(71) Applicant: Medtronic Xomed, Inc., Jacksonville, FL (US)

(72) Inventors: Osvaldo Andres Barrera, Madison, CT (US); Avram Scheiner, Vadnais Heights, MN (US); Randal C. Schulhauser, Phoenix, AZ (US); Joe Sartor, Longmont, CO (US); Patrick W. Kinzie, Glendale, AZ (US); Jason C. Lee, Edina, MN (US)

(73) Assignee: Medtronic Xomed, Inc., Jacksonville, FL (US)

( * ) Notice: Subject to any disclaimer, the term of this patent is extended or adjusted under 35 U.S.C. 154(b) by 356 days.

(21) Appl. No.: 16/862,905

(22) Filed: Apr. 30, 2020

(65) Prior Publication Data
US 2021/0338153 A1 Nov. 4, 2021

(51) Int. Cl.
*A61B 5/00* (2006.01)
*G16H 20/60* (2018.01)
(Continued)

(52) U.S. Cl.
CPC .......... *A61B 5/4818* (2013.01); *A61B 5/0024* (2013.01); *A61B 5/02154* (2013.01);
(Continued)

(58) Field of Classification Search
CPC . A61B 5/4818; A61B 5/0024; A61B 5/02154; A61B 5/14503; A61B 5/14532;
(Continued)

(56) References Cited

U.S. PATENT DOCUMENTS 9,757,560 B2   9/2017 Papay
10,029,098 B2  7/2018 Papay
(Continued)

FOREIGN PATENT DOCUMENTS

EP   3071288 B1   11/2018
JP   4745033 B2 * 8/2011
(Continued)

OTHER PUBLICATIONS

International Search Report and Written Opinion of International Application No. PCT/US2021/029818, dated Aug. 12, 2021, 10 pp.
(Continued)

*Primary Examiner* — Carl H Layno
*Assistant Examiner* — Michael J Lau
(74) *Attorney, Agent, or Firm* — Shumaker & Sieffert, P.A.

(57) ABSTRACT

A sleep apnea and obesity comorbidity treatment system includes a transceiver and a control module. The control module is configured to: receive sensor data, where the sensor data is indicative of a glucose level of a patient and a ketones level of the patient, transmit the sensor data to a remote feedback device, receive feedback information from the remote feedback device based on the sensor data, and where the feedback information provides indications to the patient to maintain or alter a behavior of the patient based on the glucose level and the ketones level, and based on the feedback information, performing an operation to maintain or alter at least one of a diet or physical activity of the patient.

28 Claims, 12 Drawing Sheets

(51) Int. Cl.
 *G16H 20/70* (2018.01)
 *A61B 5/0215* (2006.01)
 *A61B 5/145* (2006.01)
 *A61B 5/1486* (2006.01)

(52) U.S. Cl.
 CPC ...... *A61B 5/14503* (2013.01); *A61B 5/14532* (2013.01); *A61B 5/14865* (2013.01); *A61B 5/4836* (2013.01); *G16H 20/60* (2018.01); *G16H 20/70* (2018.01); *A61B 2562/0219* (2013.01)

(58) Field of Classification Search
 CPC .............. A61B 5/14865; A61B 5/4836; A61B 2562/0219; G16H 20/60; G16H 20/70
 USPC ........................................................ 600/300
 See application file for complete search history.

(56) References Cited

U.S. PATENT DOCUMENTS

| | | | |
|---|---|---|---|
| 10,065,038 B2 | 9/2018 | Papay | |
| 10,744,339 B2 | 8/2020 | Makansi | |
| 2015/0283383 A1* | 10/2015 | Ternes | A61B 5/4818 607/42 |
| 2016/0015069 A1* | 1/2016 | Klein | A61K 38/168 426/601 |
| 2016/0055760 A1* | 2/2016 | Mirabile | G09B 5/06 434/236 |
| 2016/0335765 A1* | 11/2016 | Harris | G06T 11/206 |
| 2018/0116606 A1* | 5/2018 | Li | A61B 5/113 |
| 2018/0199882 A1* | 7/2018 | Klee | A61M 16/0683 |
| 2020/0269044 A1 | 8/2020 | Papay | |
| 2020/0338358 A1 | 10/2020 | Makansi | |
| 2020/0346017 A1 | 11/2020 | Caparso et al. | |

FOREIGN PATENT DOCUMENTS

| | | | |
|---|---|---|---|
| JP | 4745033 B2 | 8/2011 | |
| WO | 2019034773 A1 | 2/2019 | |
| WO | WO-2019034773 A1 * | 2/2019 | ........... A61B 5/0004 |

OTHER PUBLICATIONS

International Preliminary Report on Patentability from International Application No. PCT/US2021/029818 dated Nov. 10, 2022, 8 pp.

* cited by examiner

PERSONALIZED AND CONTEXTUALIZED TREATMENT OF SLEEP APNEA AND OBESITY COMORBIDITY

FIELD

The present disclosure relates to patient monitoring and treating systems, and more particularly, to systems for treating sleep apnea and obesity comorbidity.

BACKGROUND

This section provides background information related to the present disclosure which is not necessarily prior art.

Three types of sleep apnea are obstructive sleep apnea (OSA), central sleep apnea (CSA) and mixed apnea. Mixed apnea refers to when a patient exhibits both OSA and CSA. Sleep apnea is a disorder in which breathing is irregularly and repeatedly stopped and started during sleep, which results in disrupted sleep and reduced blood oxygen levels of a patient. OSA is caused by complete or partial collapse of the pharynx during sleep. In particular, muscles in a mouth of a patient and throat intermittently relax thereby obstructing an upper airway of the patient while sleeping. Loss of air flow causes unusual inter-thoracic pressure as the patient tries to breathe with a blocked airway. In contrast, CSA is generally the result of the cessation of a respiratory drive. This may occur, for example, when the brain of the patient fails to provide necessary signals to a diaphragm and other muscles of the patient to engage in normal breathing.

A variant of sleep apnea is upper airway restrictive/resistance syndrome (UARS). UARS is a sleep disorder characterized by the narrowing of an airway that can cause disruptions to sleep. The primary symptoms of UARS include excessive fatigue, unrefreshing sleep, difficulty concentrating, and chronic insomnia.

Sleep apnea can limit airflow in a patient and, therefore, oxygen saturation. Low oxygen saturation can lead to various further undesired conditions. Treatment of these conditions often requires an external device to assist in providing airflow. Sleep apnea can result in a lack of adequate levels of oxygen during sleep, which can contribute to abnormal heart rhythms, heart attack, heart failure, high blood pressure, stroke, memory problems, increased accidents and other negative health related conditions. Loss of sleep can occur, for example, when a person is awakened during an apneic episode.

Sleep apnea has a high rate of comorbidity with other forms of heart disease and cardiac rhythm disease. As an example, sleep apnea also has a high rate of comorbidity with obesity. Obesity is a disorder referring to when a patient has excessive body fat. Morbid obesity, defined as 100 pounds over ideal weight or a body mass index (BMI) greater than 40, significantly intersects with sleep apnea comorbidity at 77%. Obesity can occur due to, for example, (i) lack of appetite control, (ii) lack of physical ability to be active, and/or (iii) a lack of understanding of the severity of obesity. Poor sleep cycles due to sleep apnea are known to raise the ghrelin hormone, which increases appetite. Poor sleep cycles also reduce the leptin hormone, which controls feeling satiation. These hormones further affect glucose metabolism leading to further comorbidities. Poor sleep cycles are multifactorial in upsetting diet, appetite control and increasing likelihood of obesity in a patient with sleep apnea. Higher weight is a risk factor for increased obstructive sleep apnea. High weight can be associated with increased fat located in the neck area of a patient, which can reduce size and increase number of apneic episodes.

SUMMARY

This section provides a general summary of the disclosure, and is not a comprehensive disclosure of its full scope or all of its features.

A sleep apnea and obesity comorbidity treatment system is provided and includes a transceiver and a control module. The control module is configured to: receive sensor data, where the sensor data is indicative of a glucose level of a patient and a ketones level of the patient, transmit the sensor data to a remote feedback device, receive feedback information from the remote feedback device based on the sensor data, and where the feedback information provides indications to the patient to maintain or alter a behavior of the patient based on the glucose level and the ketones level, and based on the feedback information, performing an operation to maintain or alter at least one of a diet or physical activity of the patient.

In other features, the sleep apnea and obesity comorbidity treatment system further includes: a glucose sensor configured to generate data indicative of the glucose level of the patient; and a ketone sensor configured to generate data indicative of the ketone level of the patient. The sensor data includes the data generated by the glucose sensor and the data generated by the ketone sensor.

In other features, the sleep apnea and obesity comorbidity treatment system further includes: a body network device comprising the transceiver and the control module; and the remote feedback device configured to generate the feedback information and transmit the feedback information to the body network device.

In other features, at least a portion of the body network device is implanted in the patient.

In other features, the sleep apnea and obesity comorbidity treatment system further includes: a personal network device comprising the transceiver and the control module; and the remote feedback device configured to generate the feedback information and transmit the feedback information to the personal network device. The control module is configured to via the transceiver forward the feedback information to a body network device of the patient.

In other features, the sleep apnea and obesity comorbidity treatment system further includes: at least one of a 3-axis accelerometer or an impedance sensor; an electrocardiograph sensor; and an optical sensor. The control module is configured to determine an apnea hypopnea index level based on outputs of the at least one of the 3-axis accelerometer or the impedance sensor, the electrocardiograph sensor and the optical sensor, and based on the apnea hypopnea index level, alter the feedback information provided to the patient. In other features, the sleep apnea and obesity comorbidity treatment system further includes an external scale, which may be used to detect and/or provide a value indicative of a weight of the patient. The feedback information may be based on the value indicative of the weight of the patient.

In other features, the sleep apnea and obesity comorbidity treatment system further includes: at least one of a 3-axis accelerometer or an impedance sensor; an electrocardiograph sensor; and an optical sensor. The control module is configured to at least one of: determine an apnea hypopnea index level based on outputs of the at least one of the 3-axis accelerometer or the impedance sensor, the electrocardiograph sensor and the optical sensor and transmit the apnea hypopnea index level to the remote feedback device; or transmit the outputs of the at least one of the 3-axis accelerometer or the impedance sensor, the electrocardiograph sensor and the optical sensor to the remote feedback device. The control module is also configured to receive the feedback information from the remote feedback device, where the feedback information is based on at least one of the outputs of the at least one of the 3-axis accelerometer or the impedance sensor, the electrocardiograph sensor and the optical sensor or the apnea hypopnea index level. In addition the amount of therapy use is recorded by the device and transmitted as feedback information so that the compliance level of the patient can be correlated with OSA severity.

In other features, the remote feedback device is a cloud-based feedback server. The feedback information is based on sensor data collected from other patients.

In other features, the method further includes dynamically improving the feedback information to patients according to: at least one of evolution or changes in at least one of physical, physiological or psychological characteristics of the patient during treatment of the patient; and an amount of time the patient has been treated using the method and patient-specific response to the treatment and reaction to the feedback information.

In other features, a method of operating a body network device or a personal network device of a patient is provided. The method includes: receiving sensor data from sensors, where the sensor data is indicative of a glucose level and a ketones level of the patient; transmitting the sensor data from the body network device or the personal network device of the patient to a remote feedback device; receiving feedback information from the remote feedback device, where the feedback information provides indications to the patient to maintain or alter a behavior of the patient based on the glucose level and the ketones level; and based on the feedback information, performing at least one operation based the feedback information to maintain or adjust at least one of a diet or physical activity of the patient.

In other features, the method further includes: processing the sensor data at the body network device; and generating feedback information at the body network device based on results of processing the sensor data.

In other features, the method further includes: determining whether the ketones level is greater than a predetermined level; and in response to the ketone level being greater than the predetermined level, generating the feedback information to indicate to the patient that the ketone level is in great shape.

In other features, the method further includes: determining whether the ketones level is less than a predetermined level; and in response to the ketones level being less than the predetermined level, generating the feedback information to indicate to the patient to at least one of increase physical activity or eat food from a predetermined list.

In other features, the method further includes: determining whether the glucose level is greater than a predetermined level associated with fat storage for the patient; and in response to the glucose level being greater than the predetermined level, generating the feedback information to indicate to the patient to at least one of instruct the patient to perform physical activity or cease eating recently eaten food.

In other features, the method further includes: determining whether the glucose level has increased and now is decreasing indicating the patient is about to at least one of experience a crash or feel hungry; and in response to determining the glucose level has increased and now is decreasing, generating the feedback information to indicate to the patient to indicate certain types of food to prevent fat storage.

In other features, the method further includes: receiving first sensor data indicative of lung vibrations of the patient; receiving second sensor data indicative of a respiratory rate of the patient, where the sensor data received from the sensors includes the first sensor data and the second sensor data; determining an apnea hypopnea index level based on the first sensor data and the second sensor data; and generating additional feedback information based on the apnea hypopnea index level. In other features, the first sensor data and the second sensor data is detected via at least one of a 3-axis accelerometer or an impedance sensor. In other features, both a 3-axis accelerometer and an impedance sensor are used and corresponding data is blended to determine lung vibration and/or respiration rate.

In other features, the method further includes dynamically improving the feedback information to patients according to: at least one of evolution or changes in at least one of physical, physiological or psychological characteristics of the patient during treatment of the patient; and an amount of time the patient has been treated using the method and patient-specific response to the treatment and reaction to the feedback information.

In other features, a method of operating a feedback device is provided and includes: receiving sensor data from at least one of a body network device or a personal network device, where the sensor data includes data indicative of a glucose level and a ketones level of a patient associated with the at least one of the body network device or the personal network device; processing the sensor data including at least one of analyzing or evaluating the sensor data; generating feedback information based on results of processing the sensor data, where the feedback information provides indications to the patient to maintain or alter a behavior of the patient based on the glucose level and the ketones level; and transmitting the feedback information to the at least one of the body network device or the personal network device to maintain or adjust at least one of a diet or physical activity of the patient.

In other features, the method further includes: determining whether the ketones level is greater than a predetermined level; and in response to the ketone level being greater than the predetermined level, generating the feedback information to indicate to the patient that the ketone level is in great shape.

In other features, the method further includes: determining whether the ketones level is less than a predetermined level; and in response to the ketones level is less than the predetermined level, generating the feedback information to indicate to the patient to at least one of increase physical activity or eat food from a predetermined list.

In other features, the method further includes: determining whether the glucose level is greater than a predetermined level associated with fat storage for the patient; and in response to the glucose level being greater than the predetermined level, generating the feedback information to indicate to the patient to at least one of instruct the patient to perform physical activity or cease eating recently eaten food.

In other features, the method further includes: determining whether the glucose level has increased and now is decreasing indicating the patient is about to at least one of experience a crash or feel hungry; and in response to determining the glucose level has increased and now is decreasing, generating the feedback information to indicate to the patient to indicate certain types of food to prevent fat storage.

In other features, the method further includes: receiving first sensor data indicative of lung vibrations of the patient; receiving second sensor data indicative of a respiratory rate of the patient, where the sensor data received from the at least one of the body network device or the personal network device includes the first sensor data and the second sensor data; determining an apnea hypopnea index level based on the first sensor data and the second sensor data; and generating the feedback information based on the apnea hypopnea index level. In other features, the first sensor data and the second sensor data is detected via at least one of a 3-axis accelerometer or an impedance sensor. In other features, both a 3-axis accelerometer and an impedance sensor are used and corresponding data is blended to determine lung vibration and/or respiration rate.

In other features, the method further includes generating the feedback information at a cloud-based feedback server based on sensor data collected from other patients.

In other features, the feedback information that is transmitted to the body network device or the personal network device alters dietary recommendations based an apnea hypopnea index. In other features, the dietary recommendations are adjusted to minimize impact of increased hunger on the glucose level and the ketone level of the patient.

In other features, the method further includes dynamically improving the feedback information to patients according to: at least one of evolution or changes in at least one of physical, physiological or psychological characteristics of the patient during treatment of the patient; and an amount of time the patient has been treated using the method and patient-specific response to the treatment and reaction to the feedback information.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
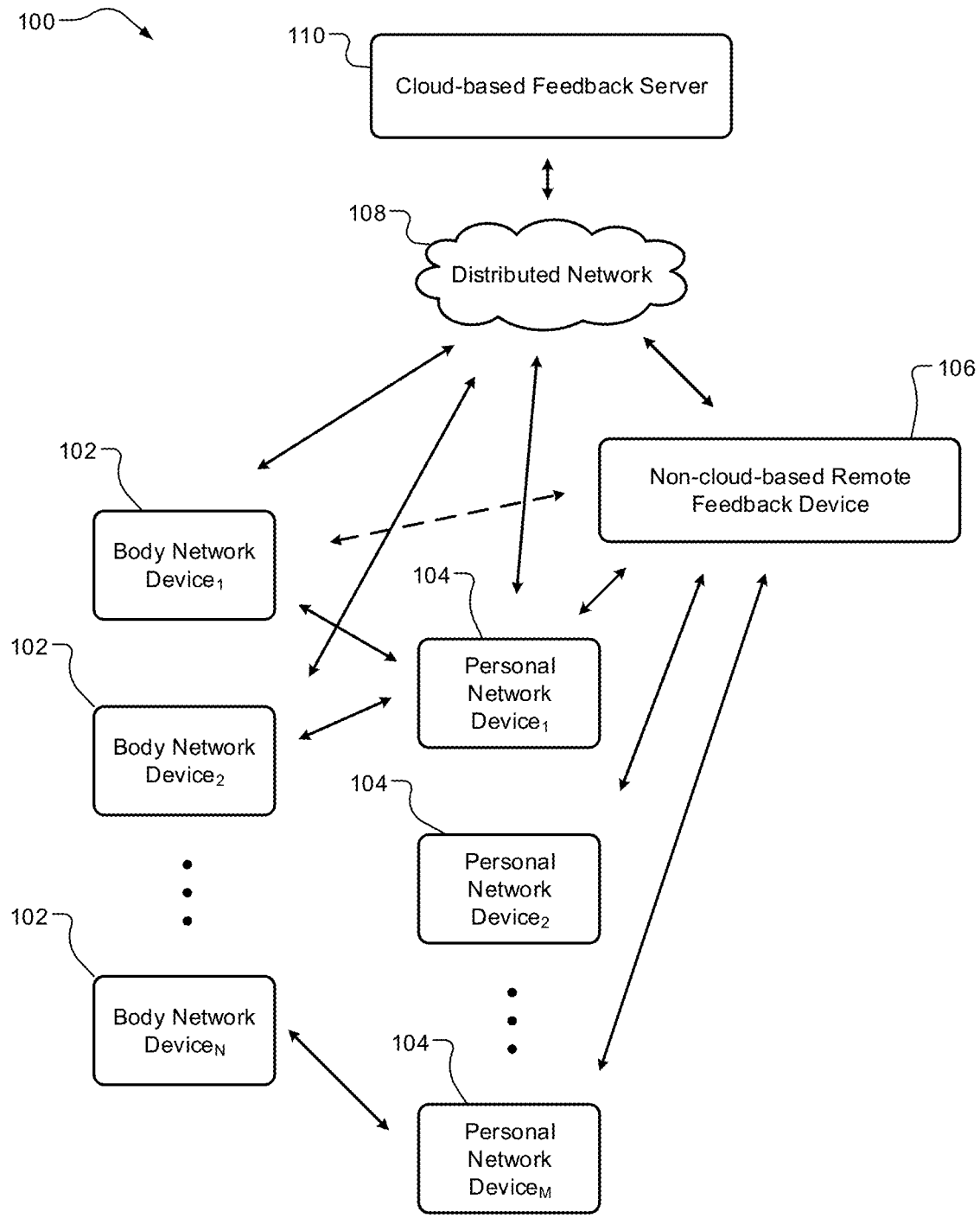
FIG. 1 is a function block diagram of an example of a sleep apnea and obesity comorbidity treatment system in accordance with the present disclosure.

Implantable medical devices capable of delivering electrical stimulation pulses exist for treating a variety of medical conditions, such as cardiac arrhythmias and chronic pain. An implantable medical device may provide stimulation pulses in, for example, a patients tongue, chest, abdomen and/or elsewhere. As an example, an OSA therapy system may implement asynchronous (i.e. non-sensing) bilateral stimulation of hypoglossal nerves. Percutaneous placement of quadripolar leads in combination with programmable stimulation channels existing in a spinal cord stimulator allow various quadripolar electrode stimulation configurations to be implemented.

The examples set forth herein include a sleep apnea and obesity comorbidity treatment system for actively detecting, treating and minimizing occurrence and/or extent of conditions associated with sleep apnea and obesity. The sleep apnea may include OSA, CSA and/or mixed apnea. There is a direct correlation between OSA and obesity. There may be an indirect correlation between CSA and obesity because of a link between obesity and heart failure and a link between heart failure and CSA.

The sleep apnea and obesity comorbidity treatment system may implement obesity management with sleep apnea therapy and is personalized to each user (or patient) and aids in changing behaviors of each patient. The sleep apnea and obesity comorbidity treatment system monitors states of the patient by sensing various aspects of the patient and provides personalized and contextual based feedback to the patient to alter the patients current state, condition, action, and/or behavior. As an example, the sleep apnea and obesity comorbidity treatment system includes glucose, ketone and apnea hypopnea index (AHI) monitoring and feedback for improved outcomes.

The AHI is the number of apneas or hypopneas recorded during the study per hour of sleep. It is generally expressed as the number of events per hour. Based on the AHI, the severity of OSA is classified as follows in Table 1:

TABLE 1

| Severity | Events |
| --- | --- |
| None/Minimal: | <5 per hour |
| Mild: | ≥5, but <15 per hour |
| Moderate: | ≥15, but <30 per hour |
| Severe: | ≥30 per hour |

In addition and/or as an alternative to monitoring the AHI, (i) oxygen desaturation levels may be monitored to indicate the severity of obstructive sleep apnea and/or (ii) a respiratory disturbance index (RDI) is monitored. Reductions in blood oxygen levels (desaturation) may be recorded during polysomnography or limited channel monitoring. At sea level, a normal blood oxygen level (saturation) is usually 96-97%. Although there are no generally accepted classifications for severity of oxygen desaturation, reductions to not less than 90% usually are considered mild. Dips into the 80-90% range can be considered moderate, and those below 80% are severe. The RDI includes apneas and hypopneas and may include other, more subtle, breathing irregularities. A RDI may be higher than an AHI.

The sleep apnea and obesity comorbidity treatment system aids in reducing patient weight and providing active sleep apnea therapy while providing enhanced therapy effectiveness and efficacy, improving patient outcomes, and providing effective value-based healthcare. A real-time (or immediate) correlation of weight to OSA, CSA and/or mixed apnea is provided.

Proper diet and exercise is considered the "Gold Standard" as the primary obesity treatment. A second tier approach includes use of prescription medications and/or diets. A third tier approach for morbid obesity non-responders includes surgical treatments such as bariatric surgery. The sleep apnea and obesity comorbidity treatment system disclosed herein causes a patient to have a lifestyle change including improving diet and increasing physical activity.

FIG. 1 shows a sleep apnea and obesity comorbidity treatment system 100 that includes body network devices 102, personal network devices 104, a non-cloud-based remote feedback device 106, a distributed network 108 and a cloud-based feedback server 110. The body network devices 102 refer to network devices located on one or more bodies of one or more users (or patients) and sense and collect data via various sensors indicating parameters, states, conditions, and/or locations of various aspects of the patients. The body network devices 102 are used to monitor biometrics, physical characteristics, locations, orientations, activity, behavior, and patterns of the patients. This includes monitoring activity patterns, eating patterns, sleeping patterns, etc.

Data collected by the body network devices 102 is shared with the personal network devices 104, non-cloud-based remote feedback device 106, and cloud-based feedback server 110. Data may be transferred from the body network devices 102 to the personal network devices 104, non-cloud-based remote feedback device 106, and cloud-based feedback server 110 directly or indirectly via the distributed network 108 and/or via one or more of the devices 104, 106. For example, data may be transmitted from the body network devices 102 to the personal network devices 104 and then from the personal network devices 104 to the non-cloud-based remote feedback device 106 and cloud-based feedback server 110. As another example, the data may be transferred from the non-cloud-based remote feedback device 106 to the cloud-based feedback server 110. The personal network devices 104 are owned and/or used by the patients of the body network devices 102. The non-cloud-based remote feedback device 106 is implemented at a health care provider office, such as an office of a doctor and/or physician of the patients. The cloud-based feedback server 110 may be implemented at a remote location away from the devices 102, 104, 106 and/or be associated with the non-cloud-based remote feedback device 106. One or more of the devices 102, 104, 106 and/or the cloud-based feedback server 110 may store, analyze, evaluate and/or provide feedback responses based on the received data and/or corresponding information.

Each of the body network devices 102 may be implemented as an implantable network device or a non-implantable network device. As an example, the body network devices 102 may be implanted in various body parts, such as heads, tongues, necks, chests, and/or abdomens of users (or patients) for which the sleep apnea and obesity comorbidity treatment system 100 is implemented. A body network device may be implanted in any appropriate location, such as in an abdominal wall, a chest wall, sub-dermally near a clavicle, or other appropriate location.

Figure 2:
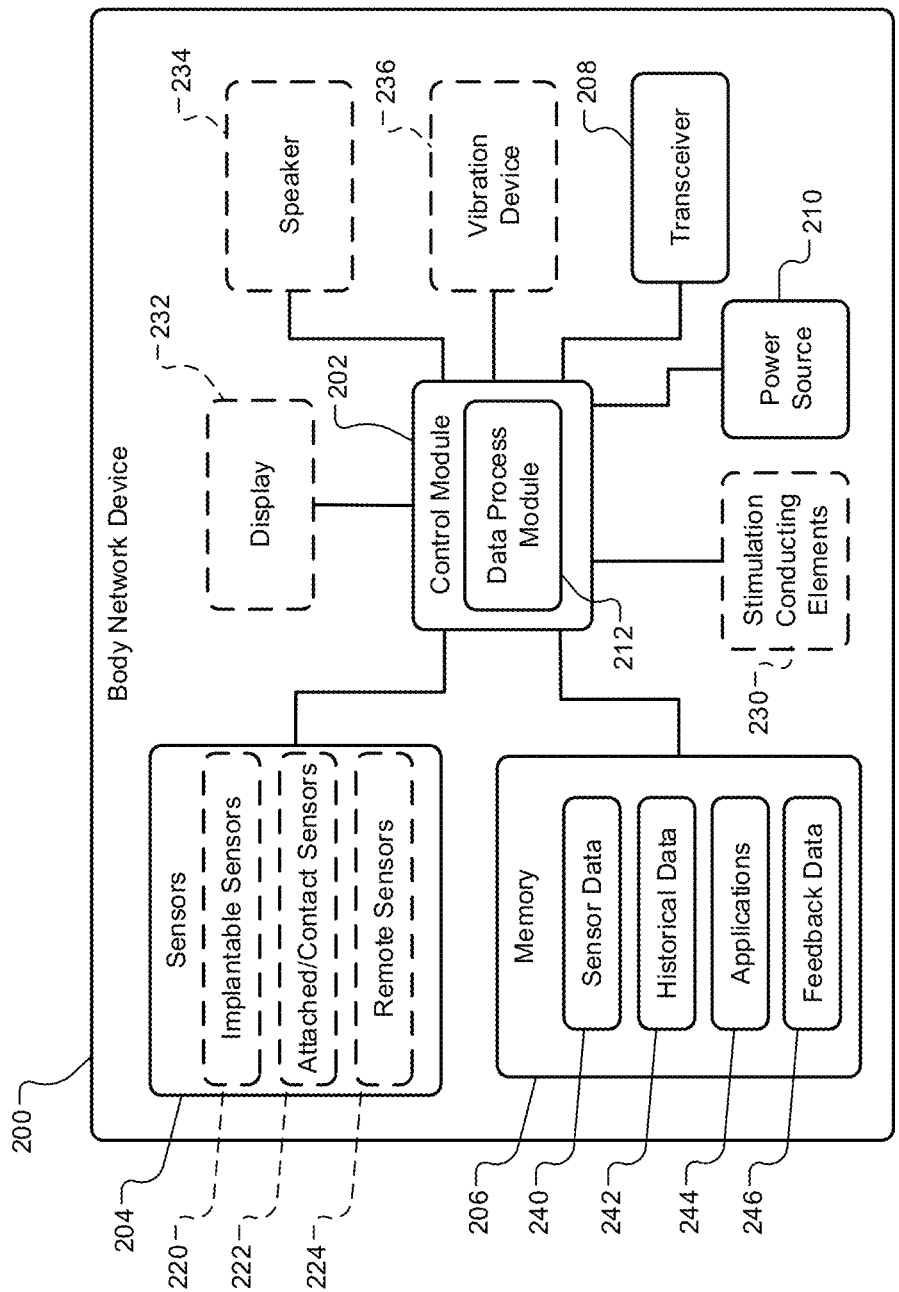
FIG. 2 is a functional block diagram of an example of a body network device of the sleep apnea and obesity comorbidity treatment system of FIG. 1.

One or more of the body network devices 102 may be implemented on, be attached to and/or be in contact with and/or be in close proximity to skin of a corresponding patient. In one embodiment, one or more of the body network devices 102 are partially implanted in a patient, where a portion of the body network device 102 extends into the patient and another portion of the body network device 102 is external to the patient. One or more of the body network devices 102 may be implemented as a wearable device, such as a watch, a ring, and/or other wearable device. An example of the body network devices 102 is shown in FIG. 2.

Figure 3:
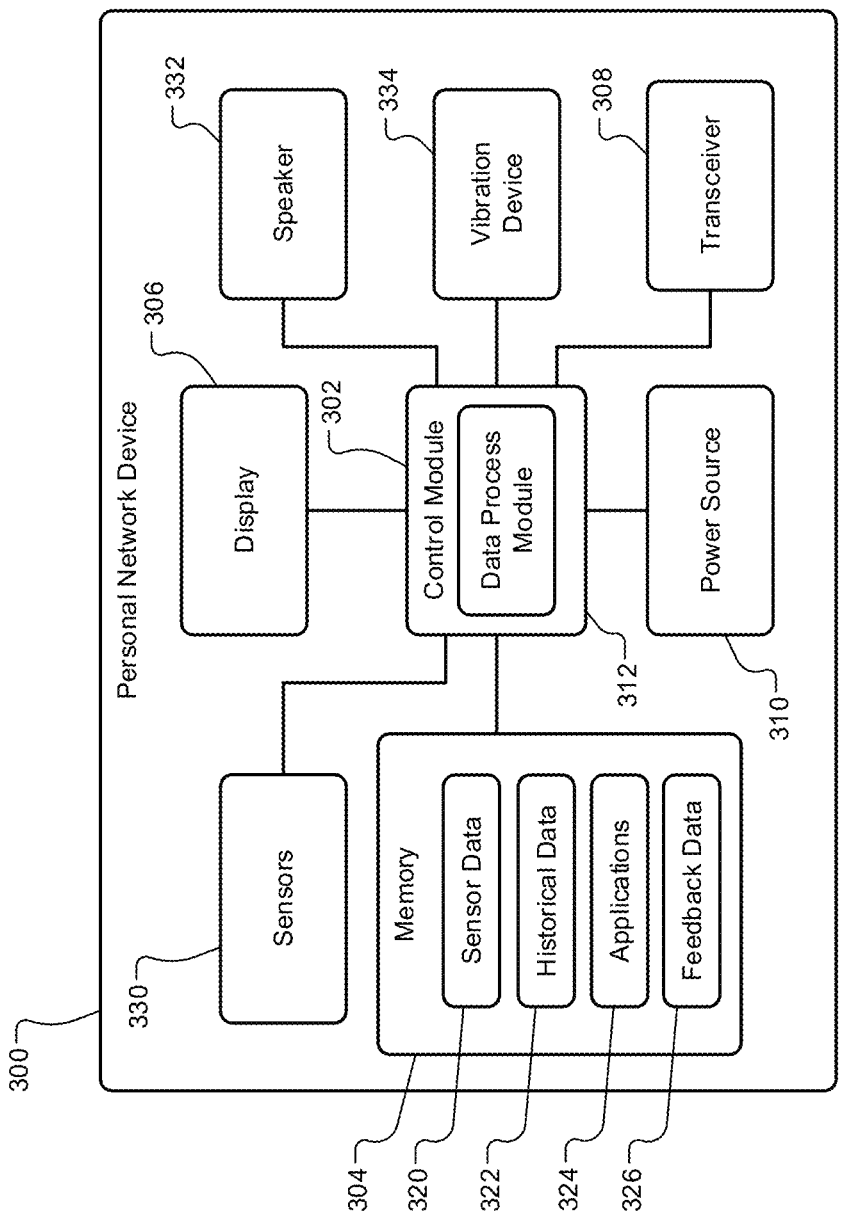
FIG. 3 is a functional block diagram of an example of a personal network device of the sleep apnea and obesity comorbidity treatment system of FIG. 1.

The personal network devices 104 may be implemented as cellular phones, tablets, notebook computers, and/or other personal portable and non-portable network devices. An example of the personal network devices 104 is shown in FIG. 3. The personal network devices 104 may be implemented as an intermediate device that connects the body network devices 102 to the non-cloud-based remote network device 106. The personal network devices 104 may provide a dashboard that conveys customized guidance to patients. The customized guidance may include guidance received in the form the feedback information from a health care provider, a doctor, a physician, etc. Examples of the customized guidance are further described below.

Figure 4:
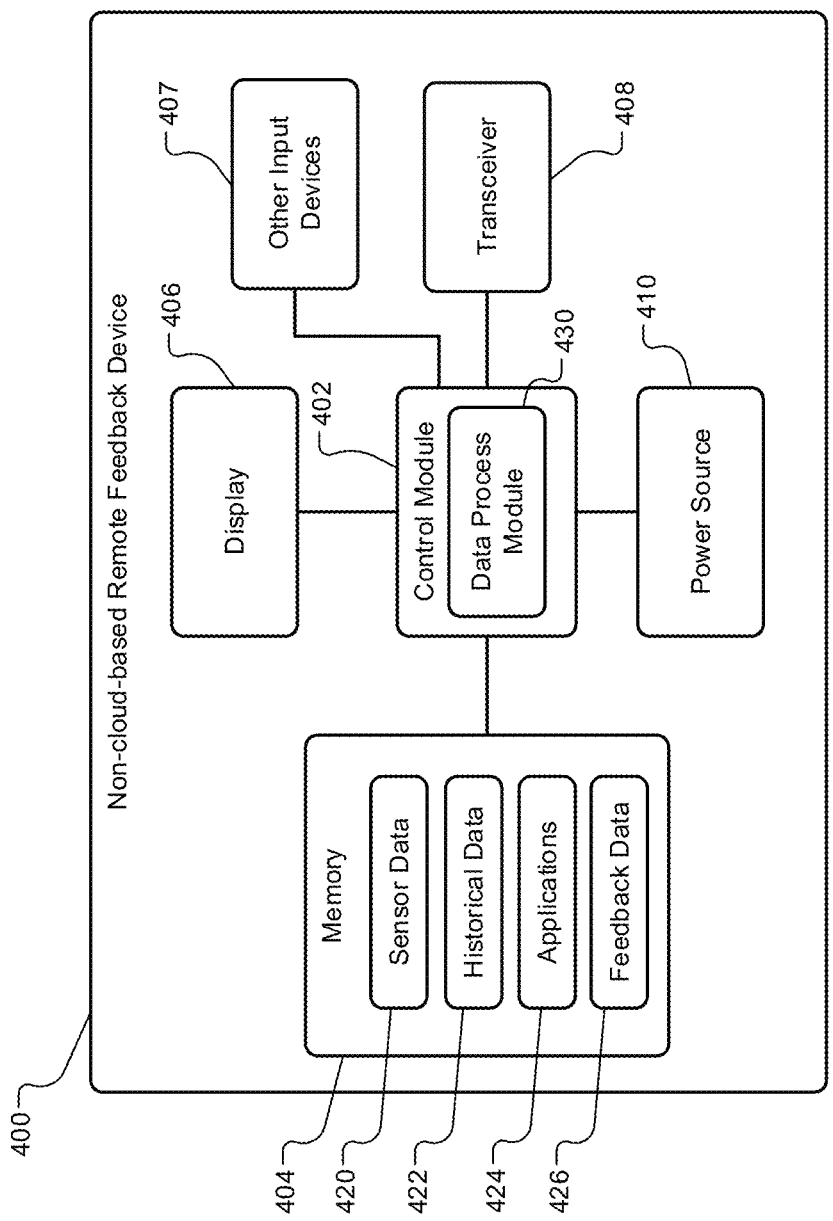
FIG. 4 is a functional block diagram of an example of a non-cloud-based remote feedback device of the sleep apnea and obesity comorbidity treatment system of FIG. 1.

The non-cloud-based remote network device 106 may be implemented as shown or may be partially or fully implemented as part of the cloud-based feedback server 110. An example of the non-cloud-based remote network device 106 is shown in FIG. 4. In one embodiment, the cloud-based feedback server 110 is partially or fully implemented as part of the non-cloud-based remote network device 106. As an example, data received from the body network devices 102 and/or the personal network devices 104 may be analyzed and/or evaluated by the non-cloud-based remote network device 106. In one embodiment, this may include a doctor, a physician or other health care person reviewing the data and/or results of an analysis performed and providing inputs. The results may include feedback information to be provided back to the body network devices 102 and/or the personal network devices 104. The non-cloud-based remote network device 106 may operate as a "health coach" to: educate; motivate; provide psychological support to resist cravings; and/or provide other feedback information to patients via the body network devices 102 and the personal network devices 104.

The feedback information may include various signals as described further below for modifying state, location, activity, eating and/or behavior of a corresponding patient. The physician may agree with the results and/or modify the results by providing inputs. The results and/or modified results may then be transmitted back to the devices 102 and/or 104. Feedback information referred to herein may refer to indications of glucose levels, ketones levels, oxygen levels, AHI values, numbers of sleep apnea events, and/or other physiological and/or biometric parameters. The feedback information may include indications as to the states of these parameters, such as whether these parameters are great, good, moderate, or poor. The feedback information may include recommendations, suggestions, and/or instructions for maintaining and/or changing behavior of a patient. The feedback information may be in the form of visual indications on a display, audio alters and/or sounds, vibration alerts, electrical stimulation, etc. The feedback information may be provided from a network device remotely located away from the patient or may be provided by a network device partially or fully implanted in the patient, in contact with the patient, and/or being used by the patient.

Figure 5:
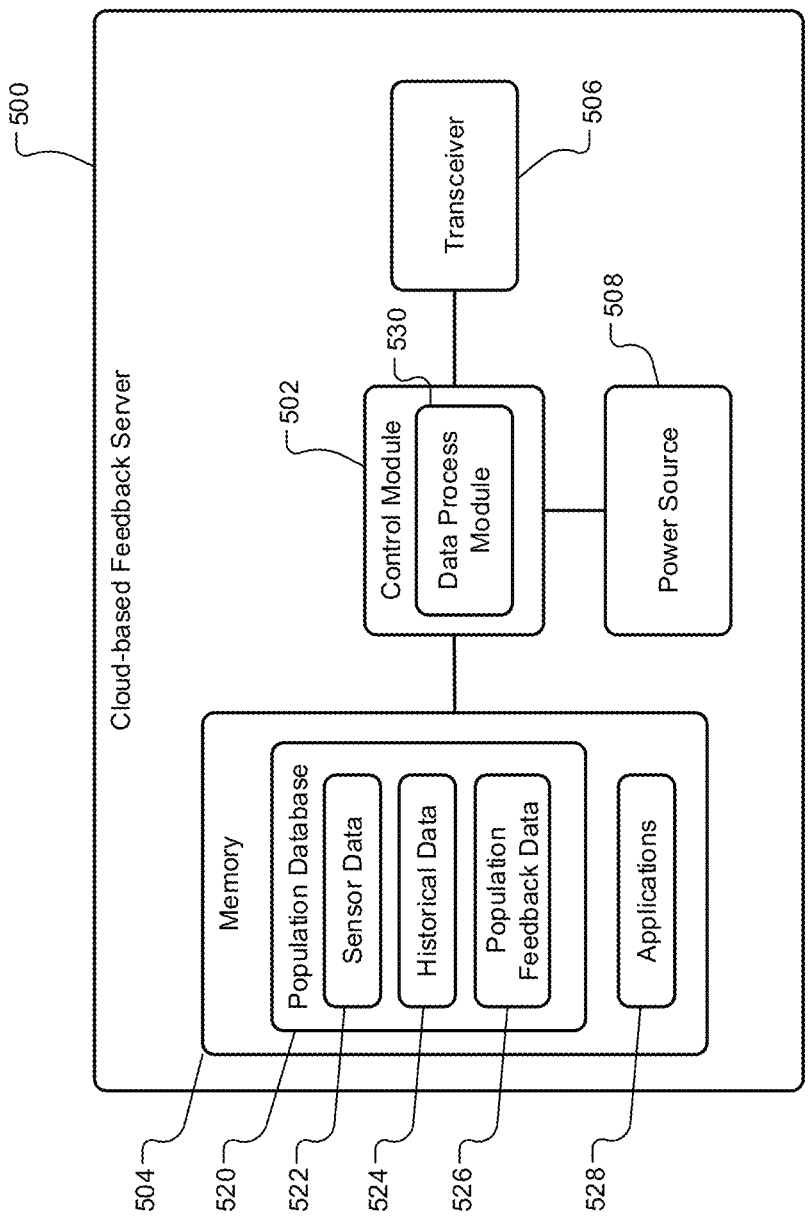
FIG. 5 is a functional block diagram of an example of a cloud-based feedback server of the sleep apnea and obesity comorbidity treatment system of FIG. 1.

The cloud-based feedback server 110 may perform similar operations as the non-cloud-based remote network device 106, but further collect data for and/or from numerous patients to provide population based updates. An example of the cloud-based feedback server 110 is shown in FIG. 5. The data collected and/or summarized by the cloud-based feedback server 110, results of data analysis performed by the cloud-based feedback server 110, and/or other related information may be shared with the non-cloud-based remote network device 106. The cloud-based sever 110 and/or the non-cloud-based remote network device 106 may transmit feedback signals to the devices 102 and/or 104 based on this data and information. The non-cloud-based remote network device 106 and/or the cloud-based feedback server 110 may analyze and/or evaluate the collected data and information using artificial intelligence processes.

In one embodiment, the non-cloud-based remote network device 106 is implemented as a cloud-based network device. Any of the body network devices 102, personal network devices 104, non-cloud-based remote feedback device 106 and/or cloud-based feedback server 110 may be referred to as a network device and/or a remote network device. Any of the personal network devices 104, non-cloud-based remote feedback device 106 and/or cloud-based feedback server 110 may be referred to as a feedback device and/or a remote feedback device.

FIG. 2 shows a body network device 200 of the sleep apnea and obesity comorbidity treatment system 100 of FIG. 1. The body network device 200 may include a control module 202, sensors 204, a memory 206, a transceiver 208 and a power source 210. The control module 202 controls operation of the body network device 200. The control module 202 may include a data process module 212, which may analyze and/or evaluate the data collected from the sensors 204 and/or other data received from the devices 104, 106 and/or the cloud-based feedback server 110 of FIG. 1. This operation may be based on data collected from the sensors 204 and data stored in the memory 206. Information collected from the sensors 204 is used to assist in determining selection of treatment for the corresponding patient.

The sensors 204 may include implantable sensors 220, attached and/or contact sensors 222, remote sensors 224, and/or other sensors including fully and/or partially implantable sensors and/or non-implantable sensors. The implantable sensors may be partially and/or fully implantable. The sensors may wirelessly or via electrically conductive elements transfer data in the form of signals to the control module 202. The sensors 204 may include a glucose sensor (a continuous glucose monitoring system (CGMS)), a metabolic sensor such as a ketone sensor (a continuous ketone monitoring system (CKMS)), an accelerometer, an impedance sensor, a cardiac rhythm or electrocardiograph (ECG) sensor, an optical sensor, an oxygen sensor, a position (e.g., relative to gravity) sensor, a body orientation sensor, and/or other sensors, some of which are referred to herein. Each of the sensors 204 may be attached to, incorporated in, and/or external to a housing of the body network device 200. The sensors 204 may include a weight sensor, such as an external weight sensor for detecting weight of the patient. The position and/or body orientation sensors may include accelerometers, global positioning sensors and/or other position and/or motion sensors. The position and/or body orientation sensors may be implemented as part of a global position system. The sensors 204 may include an oximeter and/or an electromyography sensor, The sensors 204 may be external or wearable sensors, which may be placed in various locations on the patient. The sensors 204 may include a temperature sensor, a carbon dioxide ($CO_2$) detector, an airflow (e.g. nasal or mouth) detector, a microphone (e.g. for detecting breathing sounds like snoring), and/or an impedance detector (e.g. to detect lung volume). A reduction in the number of snoring events and/or amplitude (dB) is likely to be associated with improvements in the patient's condition. Corroborating this with other parameters measured, allows the disclosed system to provide positive feedback, positive reinforcement, encouraging messages such as congratulations in meeting milestones, etc. to the patient. Snoring may be captured by accelerometers and/or microphone.

Further, various sensors may be used to determine or monitor "quality of sleep" such as sensing via electroencephalogram (EEG) type sensors and/or other sensors already mentioned. A quality of sleep determination may be correlated to OSA therapy effectiveness. Regardless of the type, the sensors 204 may also communicate with the control module 202 and/or other portions of the sleep apnea and obesity comorbidity treatment system 100 of FIG. 1.

The sensors 204 may provide information regarding a patient including: various oxygen saturation amounts (arterial or tissue oxygenation saturation amounts); muscle activation and/or activity (e.g. electromyography (EMG) activity); temperature; body position (e.g. using an accelerometer); cardiac rhythm (electrocardiograph (ECG)); and/or other appropriate parameters. A sleep study may be performed on the patient including sensing various features of the patient in a polysomnograph. One or more of the sensed elements may be sensed to assist in providing an appropriate stimulation to the patient as a part of the therapy provided. The stimulation may be provided via stimulation conducting elements 230. Depending on the type of body network device, the stimulation conducting elements may not be included. The sensors 204 may also or alternatively include inertial measurement units (IMU), fiber-Bragg gratings (e.g., shape sensors), optical sensors, acoustic sensors, pulse oximeters, etc.

The body network devices may be implemented as and/or include implantable devices for assessing and applying therapy to a patient. A few additional examples of implantable devices are pacemakers, implantable cardiac defibrillators (ICDs), and cardiac resynchronization therapy (CRTs) devices. The pacemakers and ICDs may be either single or dual chamber devices. In addition, implantable neural stimulators such as those used for the treatment of OSA by delivering therapy directly to the lingual muscles of a patient's tongue may be used. If monitoring mixed apnea, an additional lead positioned intravascularly to capture the phrenic nerve for CSA therapy may be used. In an embodiment, a combination of hypoglossal nerve stimulation and phrenic nerve stimulation is provide for mixed apnea therapy. All these implantable devices include a variety of sensors to collect various physiological data from the patient. Utilization of the data generated by these implantable devices provides an improved and largely automated system and method of assessing and treating sleep apnea in patients having these implantable devices. The body network devices may be implemented as various different types of OSA therapy devices, such as dental appliances, which operate to keep airway open and include sensors that indicate apneic events. As another example, the body network devices may include motion pillows and similar devices that cause a patient to assume a better body position to keep the airway open and send data to the other network devices indicating apneic events.

The body network device 200 may include a display 232 to show data collected, results of analysis performed, and/or other feedback information referred to herein to the patient. As an example, the display 232 may display feedback information such as dietary information, sleeping related information, exercise and/or other activity related information, etc. As another example, the body network device 200 may be implemented as a wearable device and inform the patient when body activity (e.g., walking, climbing stairs, running, working out, etc.) is being suggested. The wearable device may also or alternatively indicate when to eat and/or not eat certain foods to improve glucose and/or ketone levels. In one embodiment, the body network device 200 includes one or more other feedback devices, such as a speaker 234 and/or a vibration device 236 (e.g., an electric motor). Feedback may be provided to the patient via the speaker 234 and/or the vibration device 236.

The memory 206 may store sensor data 240, historical data 242, one or more applications 244 and feedback data 246. The sensor data 240 includes data collected via the sensors 204. The historical data 242 may include past collected sensor data and/or other data. The historical data 242 may include feedback data and/or information received from the devices 104, 106 and/or the cloud-based feedback server 110 of FIG. 1. Collected data may be compared to the historical data to determine a pattern, a trend, and/or a suggested response in the form of feedback to the patient. The applications are implemented by the control module 202 and as an example may include an application for collecting data from the sensors, an application for analyzing the data from the sensors and/or other data, and an application for providing feedback to the patient.

The transceiver 208 may include a physical layer (PHY) device and a medium access control (MAC) device and transmit signals to and receive signals from the devices 104, 106 and the cloud-based feedback server 110 of FIG. 1. The power source 210 may include, for example, a battery and supply power to the control module 202 as shown and/or to other devices of the body network device 200.

In one embodiment, the control module 202 is implemented as a therapy delivery circuit and operates as a charging circuit for delivering stimulation, via the stimulation conducting elements 230. The control module 202 may include one or more holding capacitors that are charged, via the power source 210. The holding capacitors are switchably connected to the stimulation conducting elements 230. As an example, the stimulation conducting elements 230 are implemented as a bipolar electrode pair. The holding capacitors may be charged to a programmed pacing pulse and discharged for a programmed pulse width. The control module 202 may include capacitor charge pumps or an amplifier for a charge source to enable rapid recharging of the holding capacitors. The control module 202 may provide therapeutic pulses, via the stimulation conducting elements 230.

The stimulation conducting elements 230 may be selectively coupled in a time-varying manner to deliver stimulation to different portions of protrusor muscles at different time to avoid fatigue, without requiring stimulation to be withheld completely. The control module 202 may include a switch array, switch matrix, multiplexer, or any other types of switching devices suitable for controlling selection, pulse durations, pulse frequencies, pulse duty cycles, etc. of stimulation signals provided to the stimulation conducting elements 230. The control module 202 may select polarities, voltage or current amplitudes, pulse rates, therapy duration, and/or pattern of electrode selection for delivering patterns of pulses, via the stimulation conducting elements 230. This may be coordinated among two or more body network devices.

As an example, stimulation may be provided in a tongue of a patient. The tongue may have branches of a hypoglossal nerve therein. The hypoglossal nerve may extend from the seventh cranial nerve and into the tongue. Natural, such as through signaling from the brain and spinal cord, innervation of the hypoglossal nerve may cause movement or contraction of selected muscles in the tongue. The innervation of the hypoglossal nerve, therefore, may cause portions of the tongue to contract and/or stiffen. Phrenic nerve stimulation may be performed for CSA and hypoglossal nerve stimulation and phrenic nerve stimulation may be provided for mixed apnea.

As an example, stimulation may be provided to the phrenic nerve or diaphragm of the patient to ensure breathing is done in a continuous pattern when sleeping. As is generally understood by one skilled in the art, an OSA may occur when all or part of the tongue falls or collapses into the airway. Obstruction of the airway may reduce or eliminate passage of air (e.g. including oxygen) to the subject. The obstruction may occur during a sleep cycle of the subject and is therefore commonly referred to as OSA. A similar or related condition may be upper airway restrictive/resistance syndrome (UARS). Contraction of muscles in the tongue may cause movement of the tongue out of the airway to reduce or treat OSA and/or UARS in the subject.

In some examples, an user (such as a surgeon) may implant the one or more leads such that one or more electrodes are implanted within soft tissue, such as musculature of the tongue, proximate to selected branches, such as medial branches, of one or both hypoglossal nerves. In some examples, one or more electrodes may be approximately 5 mm (e.g., about 2 mm to about 8 mm) from a major trunk of the hypoglossal nerve. In some examples, one or more electrodes may be placed in an area of protrusor muscles of the tongue that include motor points, where each nerve axon terminates in the muscle (also called the neuro-muscular junction and/or nerve end plates). The motor points are not at one location but spread out in the protrusor muscles of the tongue. Leads may be implanted such that one or more electrodes may be generally in the area of the motor points (e.g., such that the motor points are within about 1 mm to about 10 mm from one or more electrodes).

As described above, electrical stimulation therapy generated using the stimulation conducting elements 230, which may be implemented and/or include electrodes, may activate protrusor muscles to move the tongue forward, for instance, to promote a reduction in obstruction or narrowing of the upper airway during sleep. As used herein, the term "activated" with regard to the electrical stimulation of protrusor muscles of the tongue refers to electrical stimulation that causes depolarization or an action potential of the cells of the nerve (e.g., hypoglossal nerve(s)) innervating protrusor muscles of the tongue and motor points and subsequent depolarization and mechanical contraction of the protrusor muscle cells of protrusor muscles of the tongue. In some examples, protrusor muscles of the tongue may be activated directly by the electrical stimulation therapy. The stimulation waveforms provided via the electrodes may be out of phase with one another. The phase of the two waveforms may also include some overlap, but not entirely in phase.

The sensors 204 may also include sensors for determining AHI values. For example, the sensors 204 may include a 3-axis accelerometer, an ECG sensor and an optical sensor. Airflow to and from lungs may be measured. Movement of a chest of the patient may be measured. A pressure sensor may be implanted in a mouth of the patient to measure pressure. The 3-axis accelerometer and/or the impedance sensor may be tuned to lung vibrations of the patient. Activity during sleep is an indication of arousal. The impedance sensor is used to measure chest volume and is an indicator of breathing. The optical sensor can be used to detect $O_2$ saturation, which is an indication of Apnea episodes. The electrocardiac sensor may be used to measure of heart rate and sympathetic tone, which is also a measure of arousal. The ECG sensor may be used to detect an ECG baseline shift, which is proportional to respiration rate. The optical sensor may be used to detect a pulse transmit time baseline shift, which is proportional to the respiration rate. The optical sensor may be used to detect oxygen desaturation, which may be triggered based on a predetermined frequency. The control module 202 and/or the data process module 212 may execute a blended algorithm based on outputs of the 3-axis accelerometer, the ECG sensor and the optical sensor to determine an AHI value. This may also be done by any of the control modules of any of the other network devices disclosed herein. Any of the network devices may execute the blended algorithm to provide the AHI and/or feedback information based on the AHI and share the AHI and/or feedback information with the other ones of the network devices.

The AHI values may be used to evaluate patient states and behaviors to determine whether provided feedback is decreasing the number of sleep apnea events and is increasing fat burning periods in extent and/or frequency and/or reducing fat storage periods in extent and/or frequency. If provided feedback is not providing an improvement, the feedback is modified and/or indications are provided to the patient, physician, doctor and/or health care provider such that actions can be taken. This may be done via the network devices disclosed herein. In an embodiment, the non-cloud-based network device 106 instructs one or more of the devices 102, 104 to perform a sleep study process based on received data from the sensors 204 to obtain AHI values and/or other sleep apnea information.

The sensors 204 may include a blood-oxygen saturation sensor. This may be an optical sensor and configured as either a reflectance blood-oxygen saturation sensor or a transmissive blood-oxygen saturation sensor. In the case of the transmissive blood-oxygen sensor, a light source may be formed as part of a cuff designed to surround a blood vessel. A photodetector may be configured on an opposite side of the cuff from the light source. The blood-oxygen saturation sensor may be implemented either within a body of the body network device 200 or operably connected thereto. The blood-oxygen saturation sensor may be entirely separate from the body network device 200 and simply an external sensor applied to a finger of the patient, but in communication with the control module 202.

The sensors 204 may include a motion detector. The motion detector may be an accelerometer, for example a three-axis accelerometer and be tuned to detect motion caused by movement of the patient, motion caused by a beating heart (e.g., measuring the patient's pulse), or motion caused by respiration (operation of the lungs) and others. For example, the sensors 204 may be tuned to detect movement of the patient's legs. This may include detected motion which is inconsistent with a heart rate or respiration movement and does not result in a change in posture of the patient. The three-axis accelerometer may be tuned to detect snoring. A three-axis accelerometer and/or an impedance sensor may be used as a motion detector and tuned (e.g., using one or more band pass filters) to detect lung vibrations in the patient caused by respiration.

The sensors 204 may include a posture detector, such as a 3-axis accelerometer employed to detect when the patient is in a reclined or sleeping position, is laying prone or supine, or is laying on their right or left sides. The effect of 1G of gravitational acceleration applied directly along an axis of a stationary accelerometer provides a characteristic output voltage signal having an amplitude that can be referenced or scaled as +1 for angular computation purposes. The effect of 1 G of gravitational acceleration applied in precisely the opposite or negative direction to the sensitive axis provides a characteristic output voltage signal amplitude that is referenced or scaled as −1. If the axis is oriented transverse to the direction of the gravitational force, a bias voltage level output signal should be present, and that voltage signal level is referenced or scaled as 0. The degree to which the axis is oriented away or tilted from the direction of the gravitational force can also be detected by the magnitude and polarity of the output voltage signal level deviating from the bias level scaled to 0 and below the output signal level values scaled to +1 and −1. Other scales may be employed, depending on the signal polarities and ranges employed. One or more of the sensors 204 may include a microprocessor with auto-calibration of offset error and drift (caused by temperature variation and/or other varying parameters).

The sensors 204 may include an ECG sensor. ECG is a recording of the electrical activity of the heart over a period of time. While an ECG typically employs sensors placed on the skin, an effective ECG can be employed in an implantable device wherein at least two electrodes separated by a distance (e.g., at least about 35 mm) are employed to detect electrical changes caused by the cardiac depolarization and repolarization during each cardiac cycle.

The sensors 204 may include an EEG system from which the sleep stages of the patient may be determined. The EEG may include sensors implanted in the patient and operably connected to the body network device 200. Alternatively, the sensors may be implanted in the patient and operably connected to a remote or satellite implanted device located above the shoulders of the patient and in communication with the control module 202. Still further, the sensors 204 may include a wearable set of sensors that are in communication with the control module 202.

The sensors 204 may be used to provide a corollary set of data associated with a sleep study. For example, the total sleep time (TST) can be derived by comparing the time period that the patient is in a lying down position, either prone or supine, and the time where the motion sensor detects motion consistent with a sleeping heart rate, or with motion consistent with sleeping. Once a TST is determined, sleep efficiency can also be derived by comparing the TST to the total recording time (TRT), which may be the entirety of the period that the patient is in the lying down position.

Sleep stages, as in the case of a formal sleep study might require the use of EEG data from the EEG sensors, however, arousals or awakenings can be derived from the posture sensor. These would be instances where the patient transitioned from one to another posture and depending on the period of time between the beginning of the transition the transition can be characterized as an arousal or awakening. Gross motion data from a motion sensor, consistent with for example walking to the bathroom, or other data can also be overlaid on the data from the posture detector to further assist in classifying the detected movements or change in posture as an awakening or an arousal.

Respiration rate may be derived by a number of methods. As noted above, a 3-axis accelerometer and/or an impedance sensor may be tuned to the vibrations of the lungs. By such tuning, the change in position can be plotted and normalized to provide a respiration rate for the patient. Further ECG data, as might be acquired from ECG sensors is known to be proportional to respiration rate. In this way as the ECG baseline shifts, as a result of increased heart rate, a proportion change in respiration rate can be determined. Similarly, an optical sensor, such as the reflectance blood-oxygen saturation sensor described above to measure blood-oxygen saturation levels may also be employed to determine a pulse transit time. A shift in this transit time is also known to be proportional with a chance in respiration rate. For both the ECG baseline and optical sensor baseline shifts, a normal range of both of these values for the patient while sleeping may be required to determine these changes in respiration rate.

With respect to the respiration rate, any or all of these respiration rates may be employed to develop an AHI value. By comparing changes in the lung vibration, and changes in the baseline of the ECG and pulse transit times, an initial approximation of instances of an apnea can be identified. When any of these occur, the blood-oxygen saturation level sensor can be triggered to record the blood-oxygen saturation level for a given period of time following the event (assuming it is not being constantly monitored). Where a change in respiration rate is observed, if it is followed by a drop in blood-oxygen saturation level, it can reasonably be identified as an apnea, as described above with respect to Table 1. As those are measured on any given night's sleep and over the course of days, weeks, and years the development of and the incidence of sleep apnea can be assessed and actively monitored by health care providers in coordination with the treatment of the comorbid heart conditions.

As noted elsewhere, one or more of the sensors including the EEG sensors, the leg movement sensors, the ECG sensor, the blood-oxygen saturation level sensor, and others may be external to the patient and the body network device 200 without departing from the scope of the disclosure. These external sensors may be in communication the control module 202 or directly with a remote network device, such as one of the network devices 104, 106 and/or the cloud-based feedback server 110 (e.g., a cloud-based data system).

Feedback may be provided to the patient on, for example, a periodic basis including hourly, daily, weekly, bi-weekly, and/or monthly. The control module 202 may request that the patient input various self-reporting data, which may be stored and/or included with the sensor data and/or feedback data.

In one embodiment, the sensors 204 include a motion sensor, a heart rate detector, an ECG sensor, an EEG sensor, a posture detector, a blood-oxygen saturation detector, a respiration rate detector, and/or a leg movement sensor. These sensors may be formed of various sub-components including, but not limited to accelerometers tuned to detect specific types of movement and vibrations as referred to herein.

As another example, posture detection data, either alone or in combination with heart rate or respiration rate, a sleep start time and sleep end time may be determined and stored as sensor data. Using one or more accelerometers and a variety of filters, position, activity (arousals vs awakenings), sleep stages, respiration rate, and heart rate can be detected and/or determined.

The applications 244 may be executed to analyze and evaluate the data collected and assess whether the patient shows indications of suffering from sleep apnea, is in a fat burn state, is in a high glucose state, is in a low ketones state, etc. For example, a patient who registers a low sleep efficiency (TST/TRT) value, a relatively high number of arousals or awakenings, an AHI value of greater than 15, and drops in blood-oxygen saturation levels following each occurrence of an apnea would provide strong indication that the patient suffers from at least moderate sleep apnea. The application running may analyze these and other data and report an assessment to a health care provider or directly to the patient.

As another example, where the body network device is or includes a pacemaker, the network devices disclosed herein may periodically analyze the heart rhythms and interventional actions of the pacemaker. The network devices may alert the patient and/or a health care provider of heart related data (heart rates, heart rhythms, blood pressure, etc.) related directly to the body network device.

FIG. 3 shows a personal network device 300 of the sleep apnea and obesity comorbidity treatment system 100 that includes a control module 302, a memory 304, a display 306, a transceiver 308 and a power source 310. The control module 302 controls operation of the personal network device 300 and may include a data process module 312. The memory 304 may store sensor data 320, historical data 322, applications 324, and feedback data 326. The applications 324 are implemented by the control module 302 and as an example may include: an application for collecting sensor data; an application for analyzing the data from the sensors and/or other data; and an application for providing feedback to the patient.

The personal network device 300 may include sensors 330, such as cameras, a microphone, position sensors, scale sensors, weight sensors, etc., which may also be used to detect states, positions, body orientation, breathing, and/or other patient related information. The sensors 330 may also include other sensors, such as one or more of the non-implantable sensor types mentioned above for the body network device 200 of FIG. 2. The data collected from the sensors 330 may be combined with data collected from sensors (e.g., the sensors 204 of FIG. 2) of one or more body network devices and stored in the memory 304 as sensor data 320. The sensor data 320 may be shared with the devices 102, 106 and the cloud-based feedback server 110 of FIG. 1. The data process module 312 may analyze and/or evaluate the sensor data 320 and provide feedback to one or more of the body network devices 102 of FIG. 1 and/or directly to the patient via the display 306, a speaker 332, and/or a vibration device 334 (e.g., an electric motor).

The transceiver 308 may include a PHY device and a MAC device and transmit signals to and receive signals from the devices 102, 106 and the cloud-based feedback server 110 of FIG. 1. The power source 310 may include, for example, a battery and/or battery pack and supply power to the control module 302, as shown and/or to other devices of the personal network device 300.

FIG. 4 shows a non-cloud-based remote feedback device 400 of the sleep apnea and obesity comorbidity treatment system 100 of FIG. 1 that includes a control module 402, a memory 404, a display 406, other input devices 407, a transceiver 408 and a power source 410. The non-cloudbased remote feedback device 400 may be a tablet, a notebook computer, a desktop computer, a work station, and/or other network device accessible to, for example, a physician. The memory 404 may store sensor data 420, historical data 422, applications 424 and feedback data 426. The sensor data 420 may include sensor data from any of the body network devices and/or personal network devices referred to herein. The historical data 422 may include historical data collected by the control module 402 or data collected by the cloud-based feedback server 110 and shared with the control module 402. The control module 402 may include a data process module 430 that analyze and/or evaluates the data collected and provides feedback to the body network devices 102 and/or personal network devices 104 of FIG. 1.

The transceiver 408 may include a PHY device and a MAC device and transmit signals to and receive signals from the devices 102, 104 and the cloud-based feedback server 110 of FIG. 1. The power source 310 may include, for example, a battery, a battery packet and/or power source components that receive power from an external source (e.g., utility power source) and supply power to the control module 402 as shown and/or to other devices of the non-cloud-based remote feedback device 400.

FIG. 5 shows a cloud-based feedback server 500 of the sleep apnea and obesity comorbidity treatment system 100 that includes a control module 502, a memory 504, a transceiver 506 and a power source 508. The memory 504 may include a population database 520 that includes sensor data 522, historical data 524, and population feedback data 526. The memory 504 may also store applications 528 implemented by the control module 502. The control module 502 may include a data process module 530.

The sensor data 522 may include sensor data from any of the body network devices, personal network devices, and/or non-cloud-based remote feedback device referred to herein. The historical data 524 may include historical data collected by the control module 502 from any of the body network devices, personal network devices, and/or non-cloud-based remote feedback device referred to herein. The data process module 430 analyzes and/or evaluates the data collected and provides feedback to the body network devices 102, the personal network devices 104 and/or the non-cloud-based remote feedback device 106 of FIG. 1.

The transceiver 506 may include a PHY device and a MAC device and transmit signals to and receive signals from the devices 102, 104, 106 of FIG. 1. The power source 510 may include, for example, a battery, a battery pack, and/or power source components that receive power from an external source (e.g., utility power source) and supply power to the control module 502 as shown and/or to other devices of the and the cloud-based feedback server 500.

Figure 6:
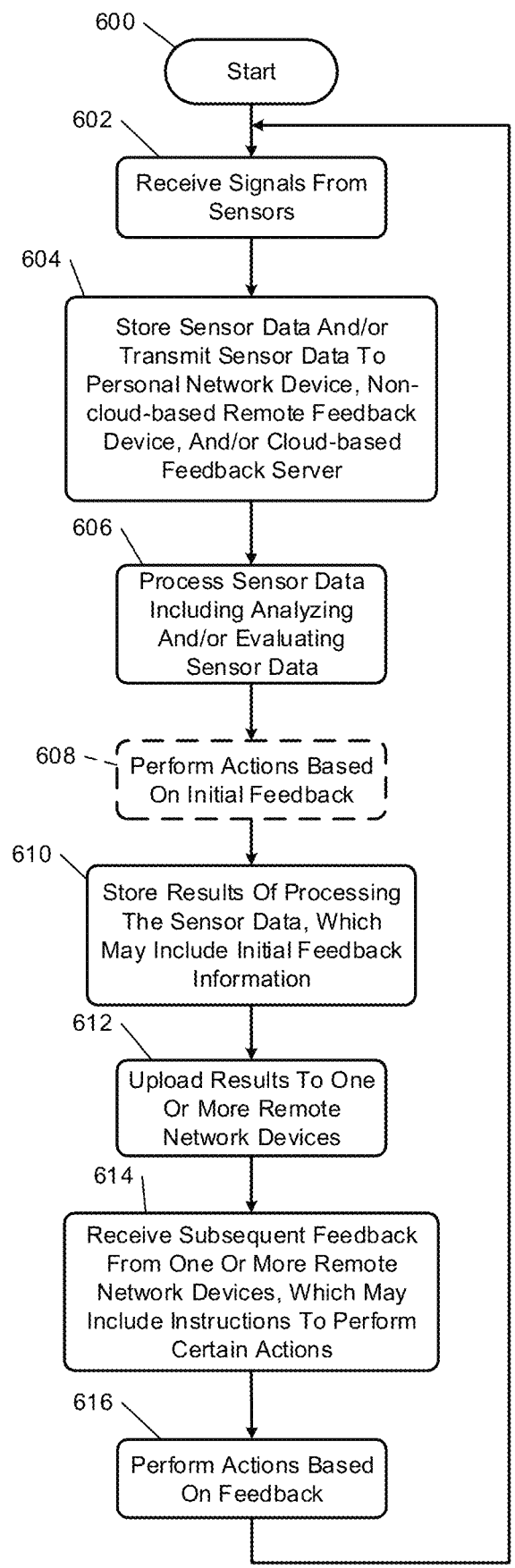
FIG. 6 illustrates a method of operating a body network device in accordance with the present disclosure.
Figure 7:
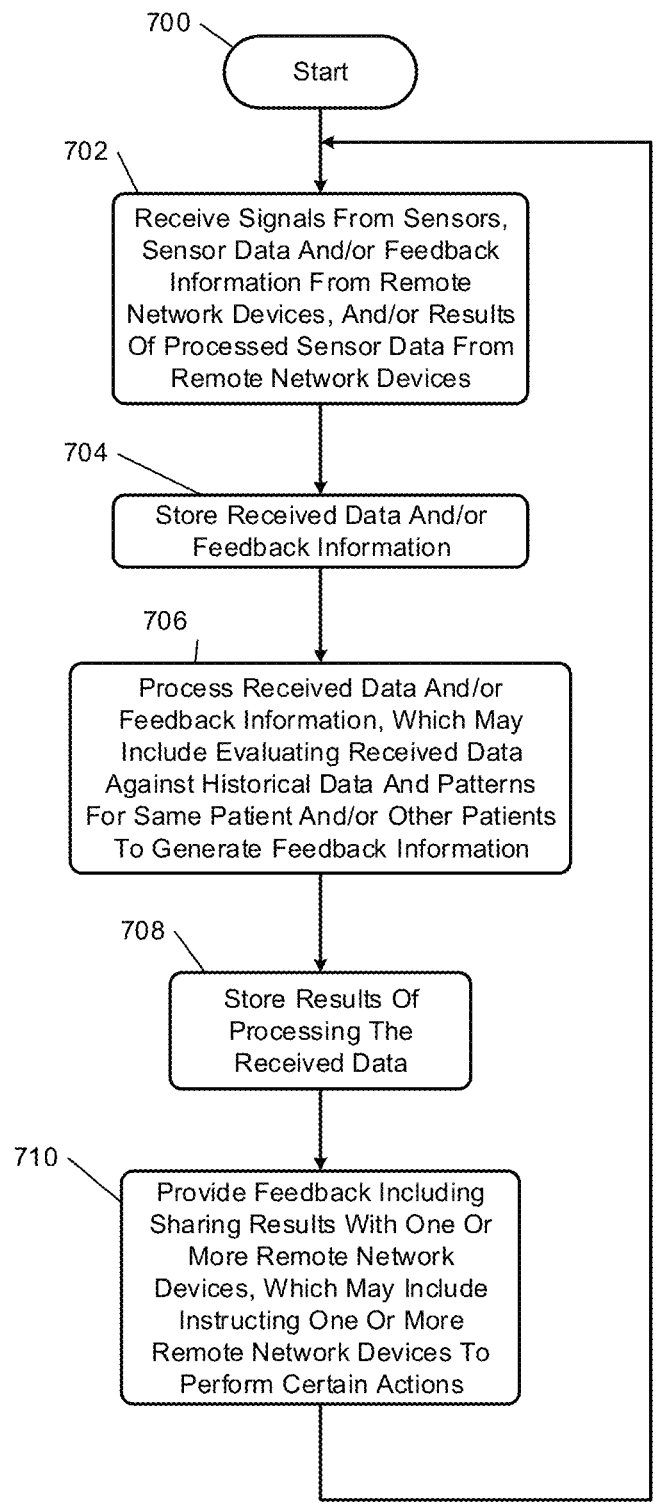
FIG. 7 illustrates a method of operating a remote feedback device in accordance with the present disclosure.
Figure 8:
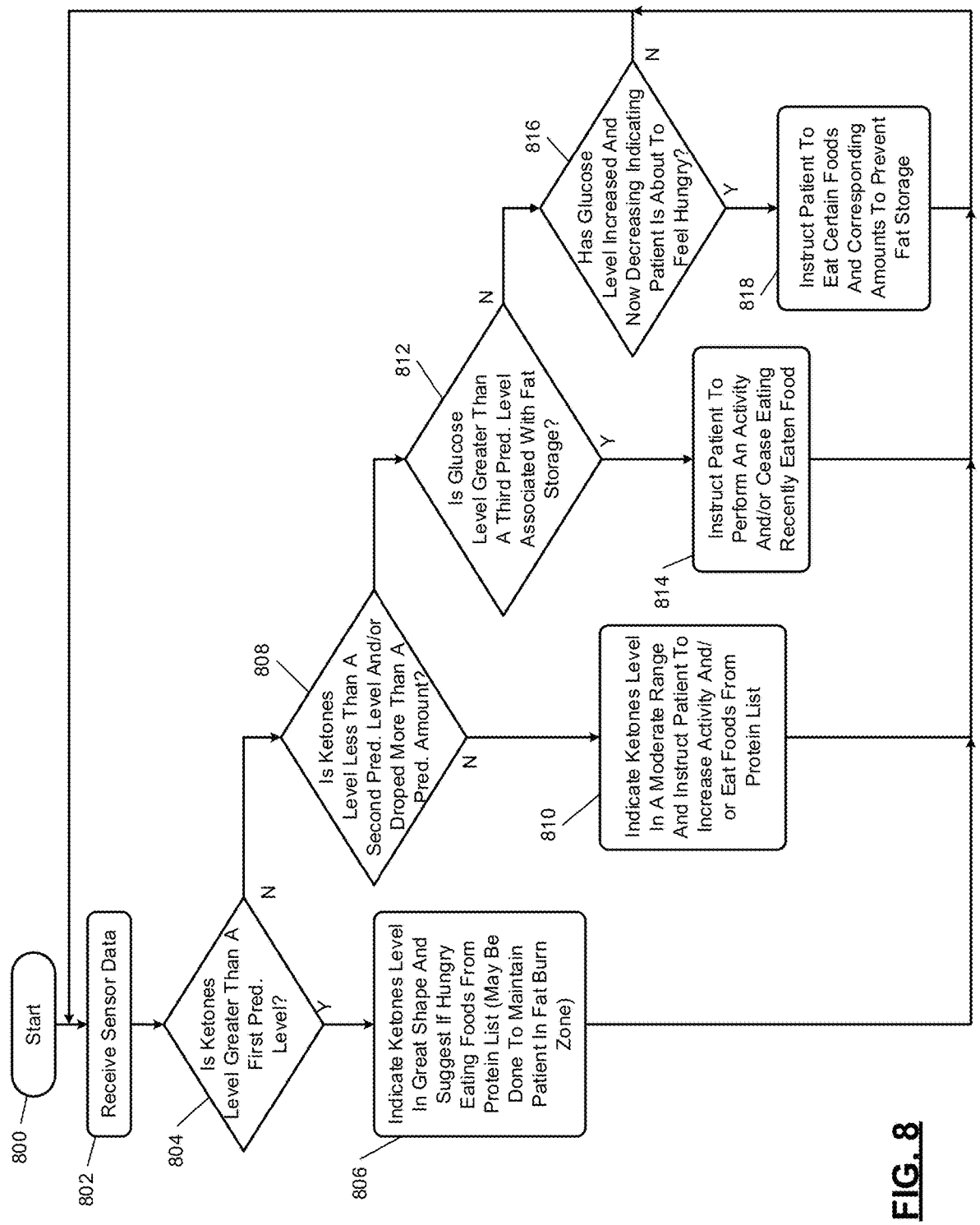
FIG. 8 illustrates a feedback method in accordance with the present disclosure.

The sleep apnea and obesity comorbidity treatment system 100 of FIG. 1 may be operated using numerous methods, example methods are illustrated in FIGS. 6-8. In FIG. 6, a method of operating a body network device (e.g., any of the body network devices 102 of FIG. 1 or the body network device 200 of FIG. 2) is shown. Although the following methods are shown as separate methods, one or more of the methods and/or operations from separate methods may be combined and performed as a single method. Although the following operations are primarily described with respect to the implementations of FIGS. 1-5, the operations may be easily modified to apply to other implementations of the present disclosure. The operations may be iteratively performed.

The method may begin at 600. At 602, the transceiver 208 monitors the sensors 204 and receives signals from the sensors 204. This may include signals from any of the sensors 204 described above. In one embodiment, this includes signals from glucose and ketone sensors and sensors associated with determining AHI values.

At 604, the control module 202 stores the signals and/or corresponding data in the memory 206. The control module 202 may also transmit the signals and/or corresponding data to one of the personal network devices 104, the non-cloud-based remote network device 106 and/or the remotely located cloud-based feedback server 110 of FIG. 1. The control module 202 may transmit the signals and/or data to one or more other body network devices of the patient.

At 606, the data process module 212 process the signals and/or corresponding sensor data and/or other sensor data received. This may include analyzing and/or evaluating the signals and/or data to provide initial feedback information similar to that described above. Operation 606 may include any or all and/or similar operations of the method of FIG. 8. At 608, the control module 202 may perform actions based on the initial feedback information.

At 610, the control module 202 stores results of the processing of the sensor data in the memory 206, which may include initial feedback information. The initial feedback information may include any of the types of feedback information referred to herein and may be indicated and/or provided to the patient via the display 232, the speaker 234, the vibration device 236 and/or the stimulation conducting elements 230. In one embodiment, a portion or all of the initial feedback information is not provided to the patient.

At 612, the results of the processing and/or the initial feedback information is provided to one or more of the network devices 104, 106, 110 of FIG. 1.

At 614, the control module 202 via the transceiver 208 receives feedback information from one or more of the network devices 104, 106, 110 based on the sensor data, process results and/or initial feedback information. The feedback information may refer to any of the feedback information disclosed herein. At 616, the control module 202 performs actions based on the feedback information. Examples of which are described herein and may include visual, audio, vibratory and/or stimulation based actions.

FIG. 7 illustrates a method of operating a feedback network device, such as one of the personal network devices 104, the non-cloud-based network device 106 and the cloud-based feedback server 110 of FIG. 1. The operations may be iteratively performed.

The method may begin at 700. At 702, signals from sensors, sensor data, and/or feedback information may be received from sensors, a body network device, a personal network device, a non-cloud-based remote network device, a cloud-based feedback server. If the feedback network device implementing the method is the personal network device 300, the control module 302 may (i) receive sensor data from the sensors 330, and/or (ii) receive sensor data and/or feedback information from the body network device 200, the non-cloud-based remote network device 400, and/or the cloud-based feedback server 500. If the feedback network device implementing the method is the non-cloud-based remote network device 400, the control module 402 may receive sensor data and/or feedback information from the body network device 200, the personal network device 300, and/or the cloud-based feedback server 500. If the feedback network device implementing the method is the cloud-based feedback server 500, the control module 502 may receive sensor data and/or feedback information from the body network device 200, the personal network device 300, and/or the non-cloud-based remote network device 400. At 704, the received sensor data and feedback information is stored in memory.

At 706, the received data and/or feedback information is processed to generate feedback information. This may include evaluating received data and feedback information against historical data for the patient and/or historical data for other patients. This is done to generate feedback information. Operation 706 may include any or all and/or similar operations of the method of FIG. 8. The indications may be provided as signals sent to one or more of the devices 102, 104.

At 708, the results of the processing performed at 706 and/or feedback information are stored in memory.

At 710, the feedback information is provided to one or more of the network devices 102 (200 in FIG. 2), 104 (300 in FIG. 3), 106 (400 in FIG. 4) and/or 110 (500 in FIG. 5) of FIG. 1. The feedback information may include any of the feedback information referred to herein. The feedback information may include diet, activity, and/or sleep recommendations, suggestions, and/or instructions.

FIG. 8 illustrates a feedback method, which may be implemented by, for example, any of the data process modules disclosed herein. The operations may be iteratively performed. The method may begin at 800. At 802, sensor data may be received as described above.

At 804, the data process module may determine whether a ketones level is greater than a first predetermined level, which may be specific to the corresponding patient. If yes, operation 806 may be performed, otherwise operation 808 may be performed.

Figure 11:
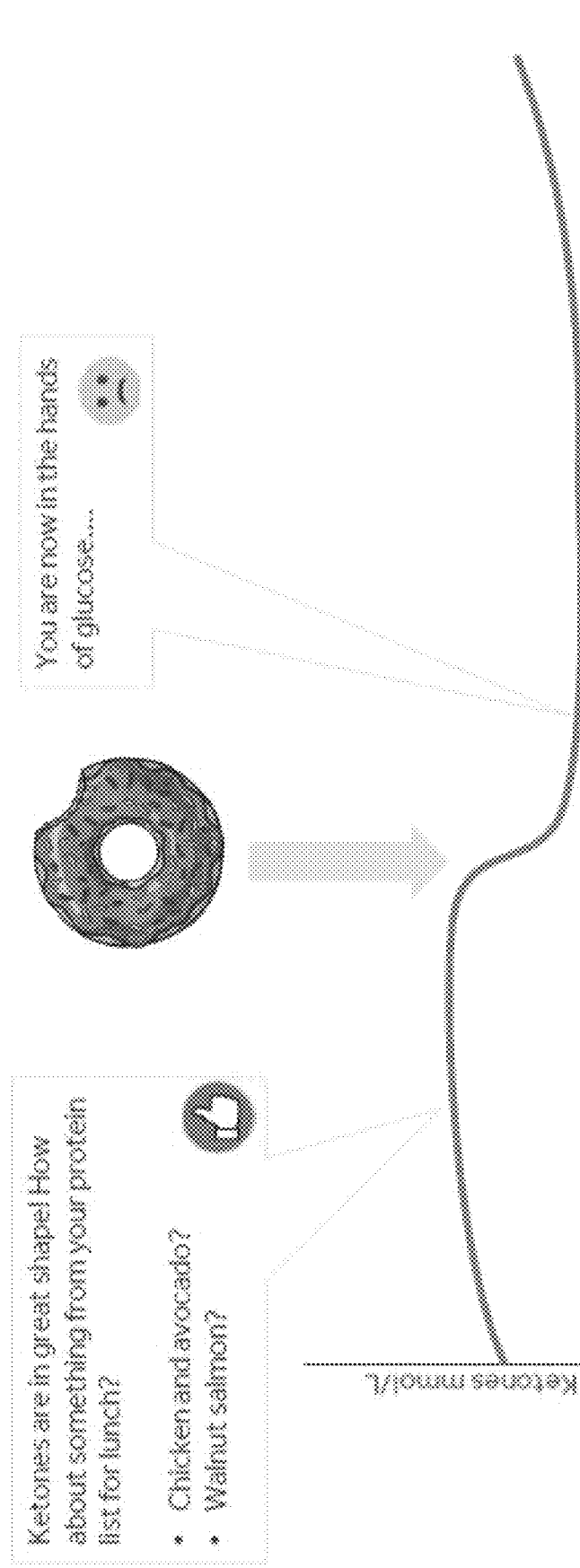
FIG. 11 is an example feedback diagram for different ketones levels of a patient in accordance with the present disclosure.

At 806, feedback may be provided to the patient indicating the ketones level is in great shape and suggest if hungry eating foods from a protein list. This suggestion may be made to maintain the patient in a fat burn zone. The protein list may include foods high in protein and low in carbohydrates. As a few examples, the protein list may include chicken, avocado, and/or walnut salmon. FIG. 11 is an example feedback diagram for different ketones levels of a patient. When the ketones level is high, the example shows providing a "Ketones are in great shape! How about something from your protein list for lunch?" indication, via the body network and/or personal network devices. This provides meaningful real-time feedback that drives lifestyle decisions and encourages ketone metabolism to reach fat loss goals. The indications to the patient, which may be received from one of the remote network devices disclosed herein coach the patient to set healthy fat loss goals. In this manner, the disclosed system performs as a health coach for the patient. The system senses ketone levels and suggests lifestyle actions to reach goals.

At 808, the data process module determines whether the ketones level is less than a second predetermined level and/or has dropped more than a predetermined amount. The second predetermined level may be less than the first predetermined level. The second predetermined level and the predetermined amount may be specific to the patient. If no, operation 810 may be performed, otherwise operation 812 may be performed.

At 810, the data process module may indicate to the patient that the ketones level is in a moderate range and instruct the patient to increase activity and/or eat foods in the protein list. The activity may include, for example, walking, jogging, running, exercising, climbing stairs, etc. FIG. 11 shows an example when the ketones level has dropped due to the patient eating something high in carbohydrates, such as a donut. The example shows the system providing an indication of "You are now in the hands of glucose . . . " with a negative symbol, such as a sad face. This indication may be provided via the body network and/or personal network devices.

At 812, the data process module determines whether a glucose level of the patient is greater than a third predetermined level associated with fat storage. The third predetermined level may be specific to the patient and be associated with the patient's body storing fat when exceeded. If yes, operation 814 is performed, otherwise operation 816 is performed.

Figure 10:
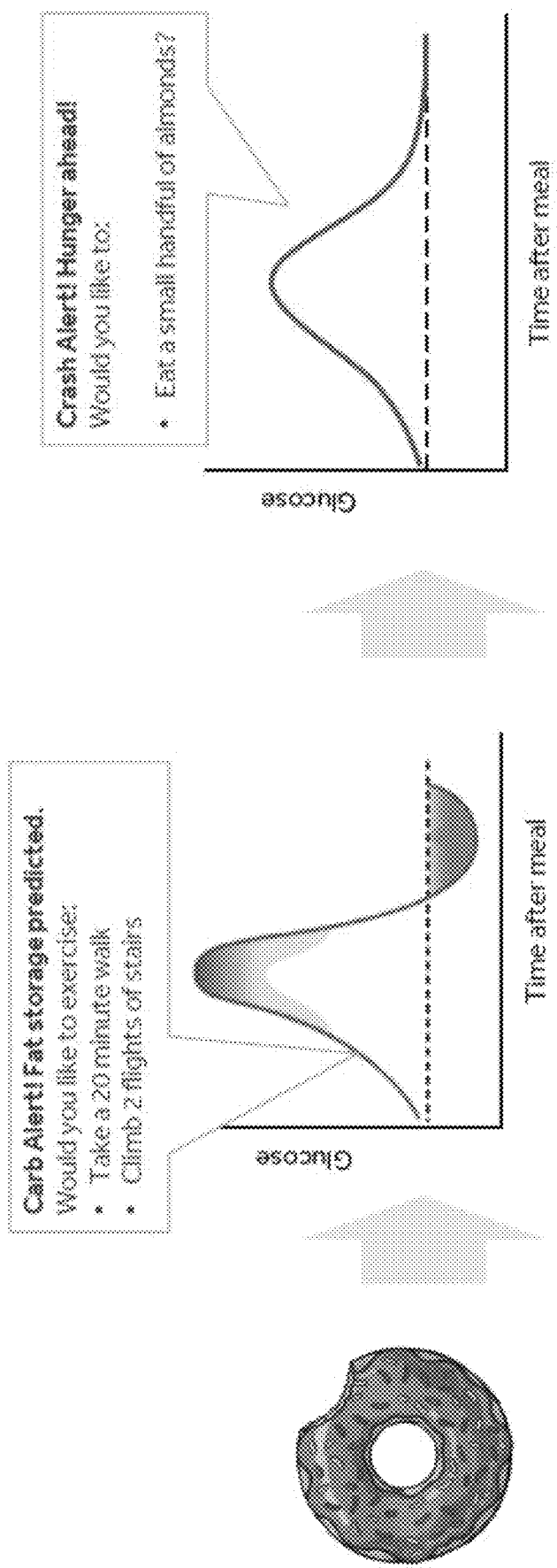
FIG. 10 is an example feedback diagram for different glucose states of a patient in accordance with the present disclosure.

At 814, the data process module may instruct the patient to perform an activity and/or cease eating recently eaten food, which may be high in carbohydrates. The activity may be any of the activities stated herein. When the glucose level is greater than the third predetermined level, fat storage is predicted. FIG. 10 is an example feedback diagram for different glucose states of a patient. As an example, a "Carb Alert!" may be shown on one or more of the body network or personal network devices of the patient indicating fat storage is predicted and to exercise for a predetermined period of time appropriate for the patient. This provides meaningful real-time feedback and drives lifestyle decisions and reduces severity of glucose spikes and crashes. Real-time suggestions promote healthy glucose control. High carbohydrate food choices trigger a glucose spike. The sleep apnea and obesity comorbidity treatment system disclosed herein senses increasing glucose levels and suggests lifestyle actions to perform via feedback using the body network and personal network devices. Negative impact of improper food choices is reduced after recommended actions are performed. This may include averting a hunger cycle.

At 816, the data process module determines whether the glucose level of the patient has increased and now is decreasing indicating that the patient is about to get hungry. If yes, operation 818 may be performed, otherwise operation 802 may be performed.

At 818, the data process module may instruct the patient to eat certain foods and corresponding amounts to prevent fat storage. FIG. 10 shows an example, when a glucose level has increased and now is decreasing indicating that the patient is about to experience a crash and feel hungry. A "Crash Alert! Hunger ahead!" indication is provided to the patient via the body network and/or personal network devices. The example, shows a feedback indication to eat a certain food to prevent and/or minimize the crash and associated effects.

All of the feedback provided in operations 806, 810, 814, 818 may be generated at and/or provided to a body network device and/or a personal network device of the patient and indicated to the patient via the body network device and/or personal network device, as described above. As another example, indications may be provided to the patient when the patient performs an action that has a negative effect. The indications may instruct the patient not to perform that action again. For example when the patient eats a certain food that causes a loss of a high ketones state and/or causes a high glucose state, the network devices may indicate not to eat the food that was recently eaten.

The above-described operations of FIGS. 6-8 are meant to be illustrative examples. The operations may be performed sequentially, synchronously, simultaneously, continuously, during overlapping time periods or in a different order depending upon the application. Also, any of the operations may not be performed or skipped depending on the implementation and/or sequence of events.

Figure 9:
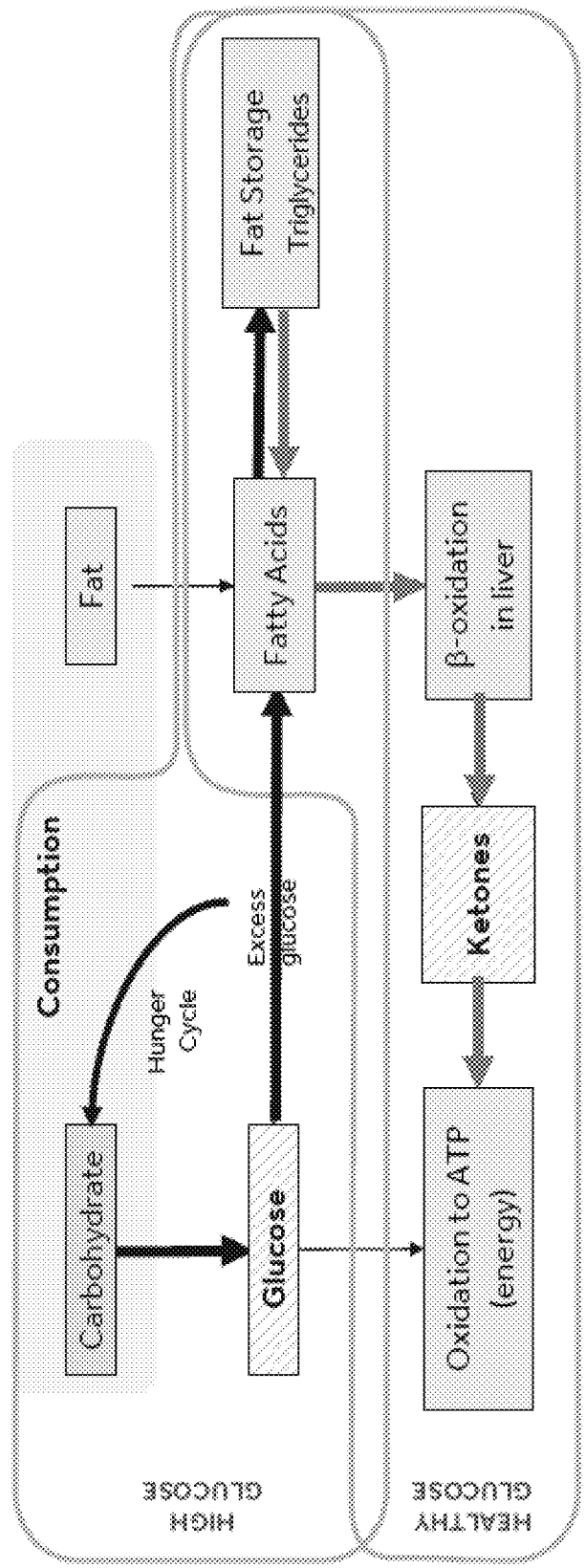
FIG. 9 is an example glucose and ketones diagram.

FIG. 9 is an example glucose and ketones diagram illustrating examples of when high glucose levels exist that cause fat storage in a body of a person versus when healthy glucose levels exist, which result in not storing fat and/or burning fat. The above-described methods aid in maintain healthy glucose levels. By controlling the glucose levels a typical hunger cycle of a person can be broken. The disclosed methods promote ketone metabolism to drive fat loss. Healthy glucose levels reflects lifestyle choices and controls the hunger cycle.

Continuous feedback based on glucose and ketone levels can drive positive long-term lifestyle modifications. Ketone levels indicate a rate of fat loss and are measureable in blood. Ketones increase with sustained glucose control and negative caloric balance and play a role in suppressing appetite. Ketones may be measured to track fat loss.

In the diagram shown, when hunger occurs and carbohydrates are consumed, glucose levels increase to create an excessive glucose condition, which creates fatty acids resulting in fat storage. When fat is ingested and carbohydrate intake is low, ketone levels increase and provide healthy glucose levels, which results in oxidation to andenosine triphosphate (ATP). ATP is an organic compound that provides energy to drive many processes in living cells and is known as the "molecular unit of currency" of intercellular energy transfer.

In the above described methods and in addition to the above-stated indications, indications may also be provided by any of the network devices to the patient and/or the health care provider that the patient may be suffering from a comorbidity of sleep apnea and obesity. Whether relying on the indication provided by the application running on the network device and/or server of the health care provider and/or based on the health care provider's own assessment of the collected data, the health care provider can initiate communications with the patient. As will be appreciated the communication can range from relying solely on the data collected to start a treatment regimen for sleep apnea to scheduling a formal sleep study.

Similarly, the applications running on the network devices of the patient can present one or more user interfaces to the patient where an initial assessment of the patient's likelihood of suffering from sleep apnea and/or obesity can be indicated. This may include an indication of a sleep score the patient received during a prior night's sleep, glucose levels and/or scores, ketones levels and/or scores, glucose plots, ketones plots, and/or historical comparisons of this and other corresponding data. Further, the user interfaces may present a suggestion to contact a health care provider, an opportunity to make an appointment with the health care provider, and/or access to emergency services if warranted.

In the above examples, a sleep apnea therapy feedback loop to obesity is described. This feedback loop may be associated with OSA therapy and/or mixed apnea therapy. It effective, the sleep apnea therapy may drive the OSA component of sleep apnea to zero leaving the patient with CSA events and thus no more mixed apnea. Since there may be an indirect correlation between CSA and obesity, the sleep apnea therapy feedback loop to obesity may also be performed to reduce CSA.

In addition, the above-described methods may include dynamically improving the feedback information to patients according to: at least one of evolution or changes in at least one of physical, physiological or psychological characteristics of the patient during treatment of the patient; and an amount of time the patient has been treated using the method and patient-specific response to the treatment (weight-loss, comorbidities, etc.) and reaction to the feedback information (type, timing, etc.).

The cloud based feedback server 110 may collect data from and/or be in communication with one or more other servers receiving similar data from other patients. The entirety of the collected data may then be analyzed by one or more neural networks to assess the combined data and to identify patterns within the data to provide indications to health care providers related to an individual patient that may require treatment and therapy. This information may be collected to provide a global assessment of a larger population of patients to the health care provider. Some of these patients will have similar comorbidities, and others will not. By further assessment of the data, the neural network can seek out similar groups of patients and provide information to health care providers regarding the likelihood of sleep apnea and obesity. This may occur before implantation of any implantable devices based on patient similarities (e.g., similarities in age, demographics, weight, heart disease, blood pressure, etc.). Further, the data from the body network devices and/or personal network devices can be constantly assessed by the neural networks to assess the population of patients having implantable devices to diagnose sleep apnea and obesity comorbidities. Additionally or alternatively, the cloud-based feedback server 110 may include one or more applications employing fuzzy logic to analyze the data from both an individual and from the broader community of patients.

As a further aspect of the present disclosure, prior to implantation of and/or monitoring of body network devices, a patient may have already undergone a patient assessment of sleep apnea and obesity with their health care provider. During this assessment a variety of self-reported issues may have been identified including daytime sleepiness, interrupted snoring, gasping, comorbidity information, etc. The data related to these issues may be stored on the cloud-based feedback server 110 as part of the patient electronic medical records (EMR), this data may also be analyzed as part of the application's assessment of the data and used when provided feedback information from any of the network devices referred to herein. Further, the EMR may include the results of a prior sleep study undertaken by the patient.

The above provide examples provide a system that may operate as a health coach for patients including implementing an artificial intelligence hardware architecture within an integrated mobile display system allowing real-time artificial intelligence processing of al patient collected data. The health coach suggestions are provided in real-time based on glucose levels, ketones levels and AHI values. A cloud-based artificial intelligence ecosystem is provided to allow population data collection and artificial intelligence processing with known interval updates to individual patient systems (e.g., boy network and/or personal network devices). The disclosed system is able to, based on patient and population updates (i.e. updates of other patients), improve OSA therapy parameters, such as stimulation patterns, duty cycles, frequencies, voltages, etc. This may be based on closed loop feedback using health coach suggestions based on the glucose, ketone and AHI related data collected. The cloud-based system may allow for better and more efficient use of health coach feedback techniques.

Since the system provides feedback based on glucose and ketones levels, the detected values do not need to be precise in order for the system to provide lifestyle improvements. The above-described system provides a personalized response and suggested diet. Each person responds to a same diet differently. The responses of different people to a same diet and/or provided feedback information is not uniform. Thus, customized lifestyle guidance is provided. Real-time biometric feedback to best personalize a person's diet is provided. This includes controlling glucose levels to control blood sugar levels and hunger, monitoring ketone bodies that indicate a level of fat burning, and/or differentiating between broken down versus consumed fat, which may be based on heart rate, patient positioning and patient movement. In one embodiment, the system operates to maintain a patient in a fat burn cycle for predetermined and/or periodic periods of time.

Figure 12:
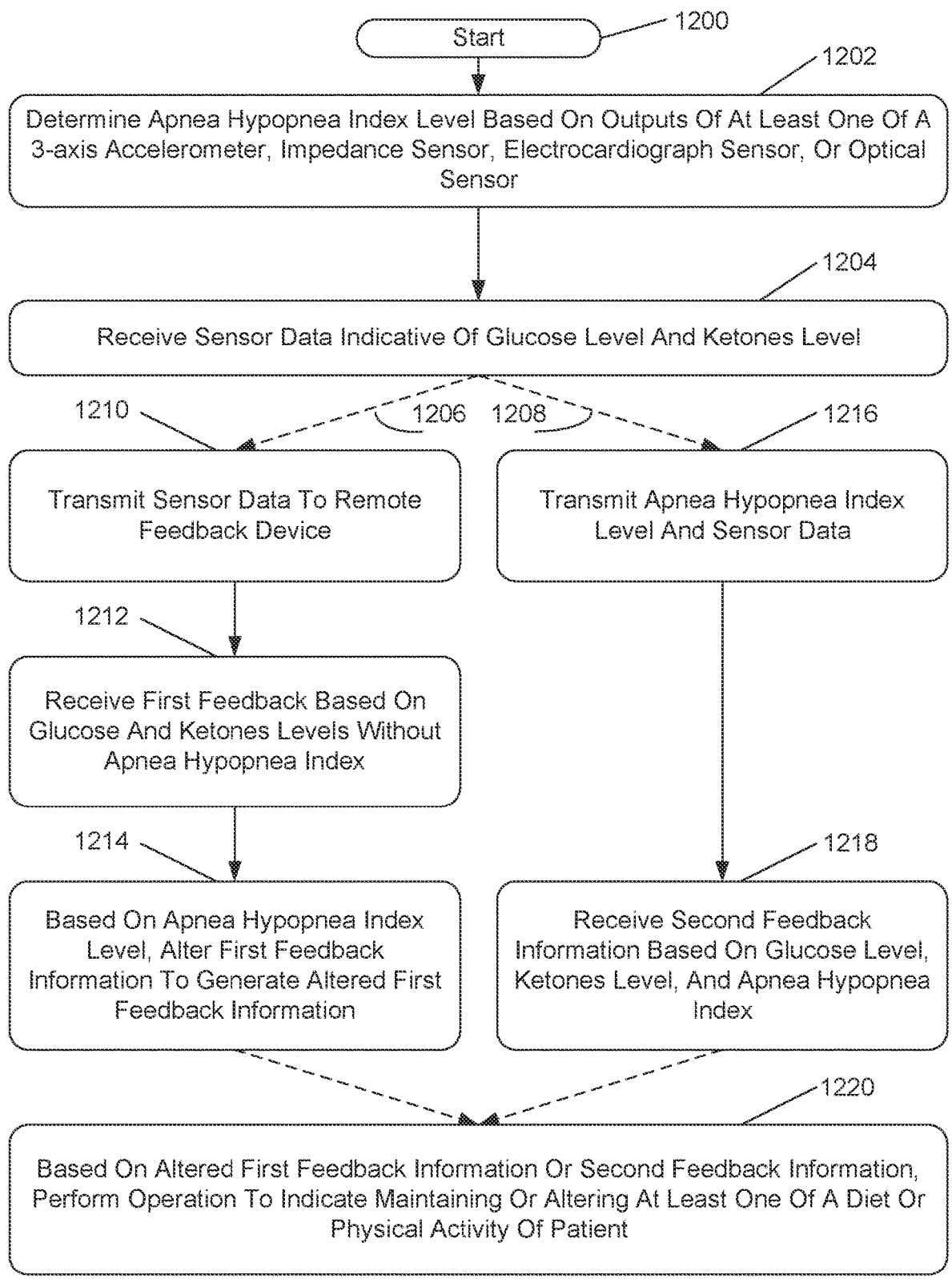
FIG. 12 is another method of operating a body network device in accordance with the present disclosure.

FIG. 12 is another method of operating a body network device in accordance with the present disclosure. The example method starts at 1200. At 1202, the control module 202 determines an apnea hypopnea index level based on outputs of the at least one of the 3-axis accelerometer, the impedance sensor, the electrocardiograph sensor, or the optical sensor. At 1204, the control module 202 receives sensor data indicative of glucose level and ketones level. For example, the control module 202 receives data from sensors 204, examples of which include a glucose sensor (a continuous glucose monitoring system (CGMS)), a metabolic sensor such as a ketone sensor (a continuous ketone monitoring system (CKMS)), an accelerometer, an impedance sensor, a cardiac rhythm or electrocardiograph (ECG) sensor, an optical sensor, an oxygen sensor, a position (e.g., relative to gravity) sensor, a body orientation sensor, and/or other sensors, some of which are referred to herein.

FIG. 12 illustrates first branch 1206 and second branch 1208 for the operation of the control 202. First branch 1206 and second branch 1208 should not be considered as being mutually exclusive. That is, in some instances, the control module 202 performs the operations of first branch 1206, and, in some instances, the control module 202 performs the operations of second branch 1208.

In the first branch 1206, at 1210, the control module 202 is configured to via transceiver 208 transmit sensor data to a remote feedback device. Examples of the remote feedback device include personal network devices 104, the non-cloud-based remote network device 106 and/or the remotely located cloud-based feedback server 110 of FIG. 1.

At 1212, as part of first branch 1206, the control module 202 receives, with transceiver 208, first feedback information that is generated based on glucose and ketones levels and without apnea hypopnea index. At 1214, as part of first branch 1206, based on the apnea hypopnea index level, the control module 202 alters the first feedback information to generate altered first feedback information. For example, as stated above, the control module 202 is configured to determine an apnea hypopnea index level based on outputs of the at least one of the 3-axis accelerometer or the impedance sensor, the electrocardiograph sensor and the optical sensor, and based on the apnea hypopnea index level, alter the feedback information provided to the patient.

At 1216, as part of second branch 1208, the control module 202 transmits, with transceiver 208, the apnea hypopnea index level and the sensor data to the remote feedback device. At 1218, as part of second branch 1208, the control module 202 receives a second feedback information from the remote feedback device. The second feedback information is generated based on the glucose level, ketones level, and apnea hypopnea index. For example, as stated above, the control module 202 is configured to at least one of: determine an apnea hypopnea index level based on outputs of the at least one of the 3-axis accelerometer or the impedance sensor, the electrocardiograph sensor and the optical sensor and transmit the apnea hypopnea index level to the remote feedback device; or transmit the outputs of the at least one of the 3-axis accelerometer or the impedance sensor, the electrocardiograph sensor and the optical sensor to the remote feedback device. The control module 202 is also configured to receive the feedback information from the remote feedback device, where the feedback information is based on at least one of the outputs of the at least one of the 3-axis accelerometer or the impedance sensor, the electrocardiograph sensor and the optical sensor or the apnea hypopnea index level.

First branch 1206 and second branch 1208 meet back at 1220. At 1220, the control module 202, based on the altered first feedback information or the second feedback information, performs an operation to indicate maintaining or altering at least one of a diet or physical activity of the patient.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A sleep apnea and obesity comorbidity treatment system comprising:
   a transceiver; and
   at least one of a 3-axis accelerometer, an impedance sensor, an electrocardiograph sensor, or an optical sensor;

a control module configured to:
  determine an apnea hypopnea index level based on outputs of the at least one of the 3-axis accelerometer, the impedance sensor, the electrocardiograph sensor, or the optical sensor;
  receive sensor data, wherein the sensor data is indicative of a glucose level of a patient and a ketones level of the patient,
  one of:
    transmit, with the transceiver, the sensor data to a remote feedback device, receive a first feedback information from the remote feedback device, wherein the first feedback information is generated based on the glucose level and the ketones level and without the apnea hypopnea index, and, based on the apnea hypopnea index level, alter the first feedback information to generate altered first feedback information, or
    transmit, with the transceiver, the apnea hypopnea index level and the sensor data to the remote feedback device, and receive a second feedback information from the remote feedback device, wherein the second feedback information is generated based on the glucose level, ketones level, and apnea hypopnea index, and
  based on the altered first feedback information or the second feedback information, perform an operation to indicate maintaining or altering at least one of a diet or physical activity of the patient.

2. The sleep apnea and obesity comorbidity treatment system of claim 1, further comprising:
  a glucose sensor configured to generate data indicative of the glucose level of the patient; and
  a ketone sensor configured to generate data indicative of the ketone level of the patient,
  wherein the sensor data includes the data generated by the glucose sensor and the data generated by the ketone sensor.

3. The sleep apnea and obesity comorbidity treatment system of claim 1, further comprising:
  a body network device comprising the transceiver and the control module; and
  the remote feedback device configured to generate the first feedback information or the second feedback information and transmit the first feedback information or the second feedback information to the body network device.

4. The sleep apnea and obesity comorbidity treatment system of claim 3, wherein at least a portion of the body network device is implanted in the patient.

5. The sleep apnea and obesity comorbidity treatment system of claim 1, further comprising:
  a personal network device comprising the transceiver and the control module; and
  the remote feedback device configured to generate the first feedback information or the second feedback information and transmit the first feedback information or the second feedback information to the personal network device,
  wherein the control module is configured to via the transceiver forward the altered first feedback information for the second feedback information to a body network device of the patient.

6. The sleep apnea and obesity comorbidity treatment system of claim 1, wherein:
  the remote feedback device is a cloud-based feedback server; and
  the first feedback information or the second feedback information is based on sensor data collected from other patients.

7. The sleep apnea and obesity comorbidity treatment system of claim 1, wherein the control module is configured to dynamically improve the altered first feedback information or the second feedback information to patients according to:
  at least one of evolution or changes in at least one of physical, physiological or psychological characteristics of the patient during treatment of the patient; and
  an amount of time the patient has been treated using the treatment and patient-specific response to the treatment.

8. The sleep apnea and obesity comorbidity treatment system of claim 1, wherein the control module performs the operation to treat at least one of obesity, obstructive sleep apnea, central sleep apnea or mixed apnea of the patient.

9. The sleep apnea and obesity comorbidity treatment system of claim 1, further comprising a sensor for detecting snoring of the patient,
  wherein the control module is configured to at least one of adjust or select the altered first feedback information or the second feedback information based on the detected snoring.

10. A method of operating a body network device or a personal network device of a patient, the method comprising:
  receiving sensor data from a plurality of sensors, wherein the sensor data is indicative of a glucose level and a ketones level of the patient;
  determining an apnea hypopnea index level based on outputs of at least one of a 3-axis accelerometer, an impedance sensor, an electrocardiograph sensor, or an optical sensor;
  one of:
    transmitting the sensor data to a remote feedback device, receiving first feedback information from the remote feedback device, wherein the first feedback information is generated based on the glucose level and the ketones level and without the apnea hypopnea index, and, based on the apnea hypopnea index level, altering the first feedback information to generate altered first feedback information, or
    transmitting the apnea hypopnea index level and the sensor data to the remote feedback device, and receiving a second feedback information from the remote feedback device, wherein the second feedback information is generated based on the glucose level, ketones level, and apnea hypopnea index; and
  based on the altered first feedback information or the second feedback information, performing at least one operation to indicate maintaining or altering at least one of a diet or physical activity of the patient.

11. The method of claim 10, further comprising:
  processing the sensor data at the body network device; and
  generating the first feedback information or the second feedback information at the body network device based on results of processing the sensor data.

12. The method of claim 10, further comprising:
  determining whether the ketones level is greater than a predetermined level; and
  in response to the ketone level being greater than the predetermined level, generating the first feedback information or the second feedback information to indicate to the patient that the ketone level is in range.

13. The method of claim 10, further comprising:
determining whether the ketones level is less than a predetermined level; and
in response to the ketones level being less than the predetermined level, generating the first feedback information or the second feedback information to indicate to the patient to at least one of increase physical activity or eat food from a predetermined list.

14. The method of claim 10, further comprising:
determining whether the glucose level is greater than a predetermined level associated with fat storage for the patient; and
in response to the glucose level being greater than the predetermined level, generating the first feedback information or the second feedback information to indicate to the patient to at least one of instruct the patient to perform physical activity or cease eating recently eaten food.

15. The method of claim 10, further comprising:
determining whether the glucose level has increased and now is decreasing indicating the patient is about to at least one of experience a crash or feel hungry; and
in response to determining the glucose level has increased and now is decreasing, generating the first feedback information or the second feedback information to indicate to the patient to indicate certain types of food to prevent fat storage.

16. The method of claim 10, further comprising dynamically improving the altered first feedback information or the second feedback information to patients according to:
at least one of evolution or changes in physical, physiological and psychological characteristics of the patient during treatment of the patient; and
an amount of time the patient has been treated using the treatment and patient-specific response to the treatment.

17. The method of claim 10, wherein the at least one operation is performed to treat at least one of obesity, obstructive sleep apnea, central sleep apnea or mixed apnea of the patient.

18. The method of claim 10, further comprising:
detecting snoring of the patient; and
at least one of adjusting or selecting the altered first feedback information or the second feedback information based on the detected snoring.

19. A method of operating a feedback device comprising, the method comprising:
receiving sensor data from at least one of a body network device or a personal network device, wherein the sensor data includes data indicative of a glucose level and a ketones level of a patient associated with the at least one of the body network device or the personal network device;
receiving information indicative of an apnea hypopnea index level that is determined based on outputs of at least one of a 3-axis accelerometer, an impedance sensor, an electrocardiograph sensor, or an optical sensor;
processing the sensor data including at least one of analyzing or evaluating the sensor data;
generating feedback information based on results of processing the sensor data and the apnea hypopnea index level, wherein the feedback information is generated based on the glucose level, ketones level, and the apnea hypopnea index, and wherein the feedback information provides indications to the patient to maintain or alter a behavior of the patient based on the glucose level and the ketones level; and
transmitting the feedback information to the at least one of the body network device or the personal network device to treat the patient including maintaining or adjusting at least one of a diet or physical activity of the patient.

20. The method of claim 19, further comprising:
determining whether the ketones level is greater than a predetermined level; and
in response to the ketone level being greater than the predetermined level, generating the feedback information to indicate to the patient that the ketone level is in range.

21. The method of claim 19, further comprising:
determining whether the ketones level is less than a predetermined level; and
in response to the ketones level is less than the predetermined level, generating the feedback information to indicate to the patient to at least one of increase physical activity or eat food from a predetermined list.

22. The method of claim 19, further comprising:
determining whether the glucose level is greater than a predetermined level associated with fat storage for the patient; and
in response to the glucose level being greater than the predetermined level, generating the feedback information to indicate to the patient to at least one of instruct the patient to perform physical activity or cease eating recently eaten food.

23. The method of claim 19, further comprising:
determining whether the glucose level has increased and now is decreasing indicating the patient is about to at least one of experience a crash or feel hungry; and
in response to determining the glucose level has increased and now is decreasing, generating the feedback information to indicate to the patient to indicate certain types of food to prevent fat storage.

24. The method of claim 19, further comprising generating the feedback information at a cloud-based feedback server based on sensor data collected from other patients.

25. The method of claim 19, wherein the feedback information transmitted to the body network device or the personal network device alters dietary recommendations based on the apnea hypopnea index.

26. The method of claim 25, wherein the dietary recommendations are adjusted to minimize impact of increased hunger on the glucose level and the ketone level of the patient.

27. The method of claim 19, further comprising dynamically improving the feedback information to patients according to:
at least one of evolution or changes in at least one of physical, physiological or psychological characteristics of the patient during treatment of the patient; and
an amount of time the patient has been treated using the treatment and patient specific response to the treatment and reaction to the feedback information.

28. The method of claim 19, wherein the feedback information is transmitted to treat at least one of obesity, obstructive sleep apnea, central sleep apnea or mixed apnea of the patient.

* * * * *